United States Patent [19]
Katti et al.

[11] Patent Number: 5,843,993
[45] Date of Patent: Dec. 1, 1998

[54] HYDROXYALKYL PHOSPHINE GOLD COMPLEXES FOR USE AS DIAGNOSTIC AND THERAPEUTIC PHARMACEUTICALS AND METHOD OF MAKING SAME

[75] Inventors: Kattesh V. Katti; Douglas E. Berning; Wynn A. Volkert; Alan R. Ketring, all of Columbia, Mo.

[73] Assignee: The Curators of the University of Missouri, Columbia, Mo.

[21] Appl. No.: 818,078

[22] Filed: Mar. 14, 1997

[51] Int. Cl.$^6$ ............................ C07F 9/02; C07F 1/12; A61K 31/28
[52] U.S. Cl. ....................... 514/495; 556/13; 556/18; 556/21; 556/110; 534/10; 514/107; 514/108
[58] Field of Search ................. 556/13, 18, 21, 556/110; 514/107, 108, 495; 534/10

[56] References Cited

PUBLICATIONS

Rush et al., (1987) In vivo and in vitro hepatotoxicity of a novel antienoplastic agent . . . *Toxicologist*, 7:59 Abstract.
Elder et al. (1981) Nearly regular tetrahedral geometry in a Gold(I) –phosphine complex. X–ray crystal structure of tetrakis . . *J. Chem. Soc. Chem. Commun.*, 900–901.
Forward et al. (1996) Synthesis and structural characterization of tetrahedral four–coordinate Gold(I) complexes . . *Inorg. Chem.* 35:16–22.
Fricker (1996) Medicinal chemistry and pharmacology of gold compounds. *Transition Met. Chem.*, 21:377–383.
Johnson (1976) in *ORTEP –A fortran thermal ellipsoid plot program*, Technical Report ORNL–5138, Oak Ridge National Laboratory, Oak Ridge, Tennessee.
Bates and Waters (1984) A tetrahedral complex of Gold(I) . The crystal and molecular structure of . . . *Inorg. Chim. Acta*, 81:151.
Berglof et al. (1978) Auranofin: an oral chrysotherapeutic agent for the treatment of rheumatoid arthritis. *J. Rheumatol.*, 5:68.
Berners–Price et al. (1984) Stable gold (1) complexes with chelate rings: solution studies of bis (phosphino) . . . *J. Chem. Soc. Dalton Trans.*, 969.
Berning et al., (1996) In vitro and in vivo characterization of 99mTc complex with tris (hydroxymethyl) phosphine (THP) *Nucl Med. Biol.*, 23:617.
Blessing (1995) An empirical correction for absorption anisotropy. *Acta Crystallogr.*, A51:33–38.
Gabe et al. (1989) NRCVAX –an interactive program system for structure analysis. *J. Appl. Cryst.*, 22:384.
Jaw et al., (1989 Crystal structures and solution electronic absorption and MCD spectra for perchlorate and halide salts . . . *Inorg. Chem.*, 28:1028.
Le Page (1988) Computer Programs. *J. Appl. Cryst.*, 21:983–990.
Le Page et al., (1979) Application of a segment dscription of the unique set of reflections to data collection . . . *J. Appl. Cryst.*, 12:464–466.
Mirabelli et al., (1985) Evaluation of the in vivo antitumor activity and in vitro cytotoxic properties of auranofin . . . *Cancer Res.*, 45:32–39.
Pitzer (1979) Relativistic effects on chemical properties. *Acc. Chem. Res.*, 12:271–276.
Pyykko (1988) Relativistic effects in structural chemistry. *Chem. Rev.*, 88:563–594.
Reddy et al. (1996a) Hydroxymethyl bis(phosphines) and their palladium(II) and platinum(II) complexes . . .*J. Chem. Soc. Dalton Trans.*, 1301–1304.
Reddy et al., (1996b) Chemistry in environmentally benign media. *Inorg. Chem.*, 35:1753–1757.
Schubiger et al., (1996) Vehicles, chelators, and radionuclides: choosing the "building blocks" . . . *Bioconjugate Chem.*, 7:165–179.
Shi et al. (1996) Chiral phosphine ligands derived from sugars. 3. Syntheses, structures, and spectroscopic properties . . *Inorg. Chem.*, 35:2742–2746.
Schmidbaur (1995) High–carat gold compounds (Ludwig Mond Lecture) *Chem. Soc. Rev.*, 391–400.
Simon et al., (1981) Screening trail with the coordinated gold compound auranofin using mouse lymphocytic . . . *Cancer Res.*, 41:94–97.
Volkert et al., (1991) Therapeutic radionuclides: production and decay property considerations. *J. Nucl. Med.*, 32:174–185.
Komiya et al., inorganica Chimica Acta, vol. 217, No. 1–2,pp. 201–202, 1994.

*Primary Examiner*—Porfirio Nazario-Gonzalez
*Attorney, Agent, or Firm*—Kohn & Associates

[57] ABSTRACT

A complex and method for making same for use as a diagnostic or therapeutic pharmaceutical includes a ligand comprising at least one hydroxyalkyl phosphine donor group bound to a gold atom to form a gold-ligand complex that is stable in aqueous solutions containing oxygen, serum and other body fluids.

16 Claims, 17 Drawing Sheets

SCHEME 1

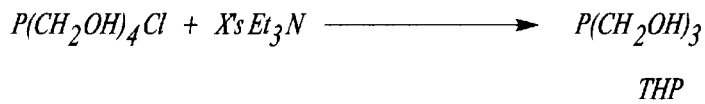

Fig-1

* HYDROXYMETHYL PHOSPHINE(S) SOLUBLE IN WATER
* OXIDATIVELY STABLE IN WATER
* FORM TRANSITION METAL COMPLEXES UNDER AQUEOUS AND BIPHASIC CONDITIONS.

SCHEME 2

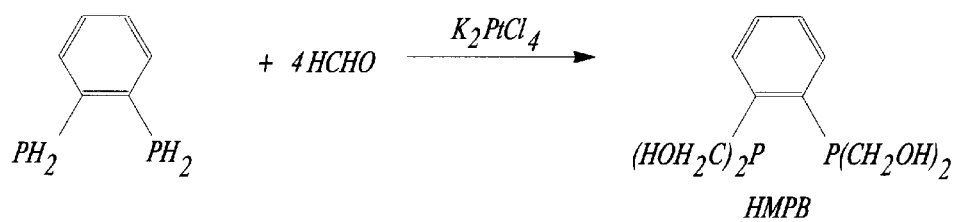

HMPB

* HYDROXYMETHYL PHOSPHINE(S) SOLUBLE IN WATER
* OXIDATIVELY STABLE IN WATER
* FORM TRANSITION METAL COMPLEXES UNDER AQUEOUS AND BIPHASIC CONDITIONS.

Fig-2

SYNTHESIS OF MONDENTATE PHOSPHINE GOLD COMPLEXES

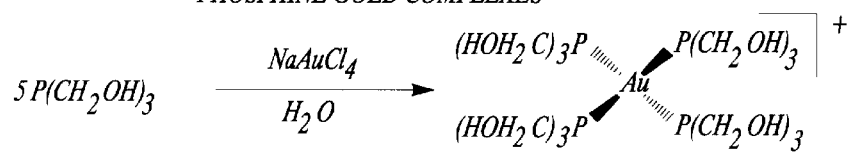

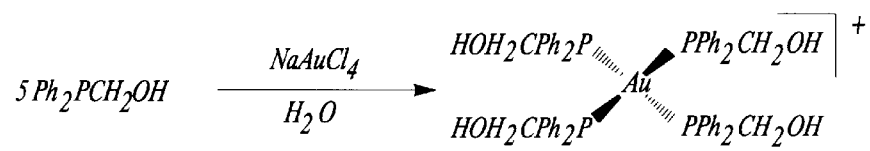

Fig-3

SCHEME 3

AuHMPB  06/28/96  18:08:26  CH="A"  PS=1

FIGURE 1: HPLC ANALYSIS OF GOLD-HMPB COMPLEX

| FILE 1. | METHOD 0. | RUN 1 | INDEX 1 | BIN 1 |
|---|---|---|---|---|
| PEAK# | AREA% | RT | AREA | BC |
| 1 | 1.791 | 7.74 | 278032 | 01 |
| 2 | 2.272 | 8.26 | 352658 | 01 |
| 3 | 0.28 | 8.82 | 43398 | 01 |
| 4 | 93.957 | 9.75 | 14587136 | 08 |
| 5 | 1.218 | 10.14 | 189027 | 06 |
| 6 | 0.483 | 10.29 | 75013 | 07 |
| TOTAL | 100. | | 15525264 | |

COLUMN: HAMILTON PRP-1, 10μm, 150 x 4.1mm
FLOW RATE: 1.0ml/min.
CHART SPEED: 0.5 cm/min.
MOBILE PHASE:
    SOLVENT A: WATER WITH 0.1% TFA
    SOLVENT B: MeCN WITH 0.1% TFA
    INITIAL 100% A
    20 min. 100% B
    23 min. 100% B
    28 min. 100% A
UV DETECTION @ 254 WITH AUFS = 2.0

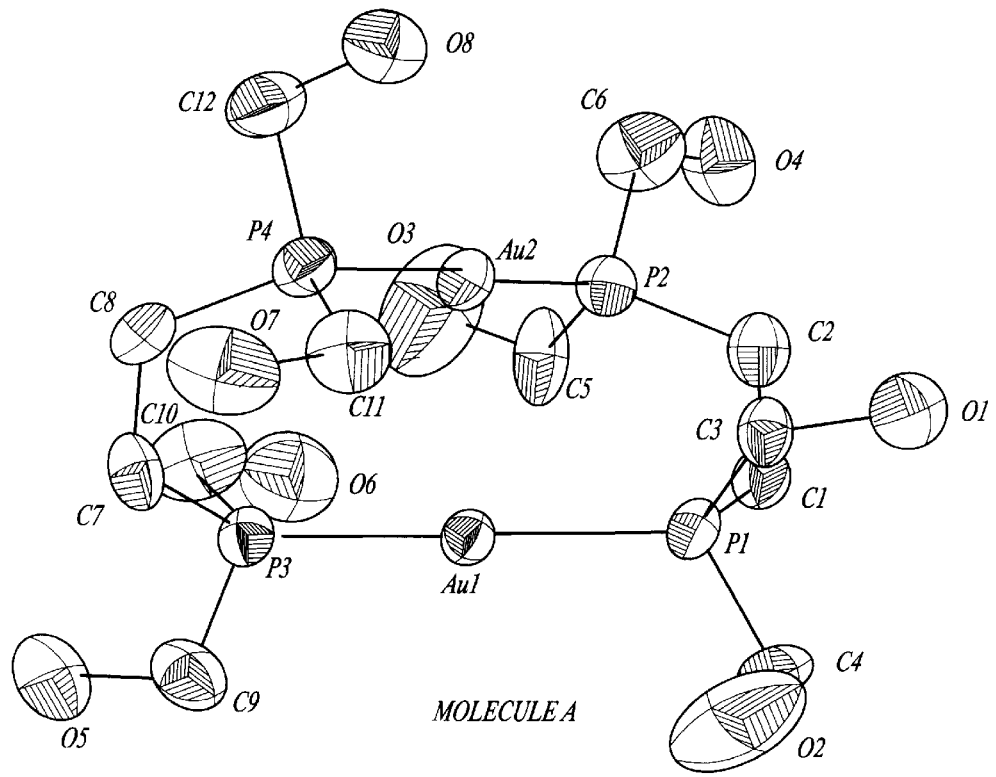
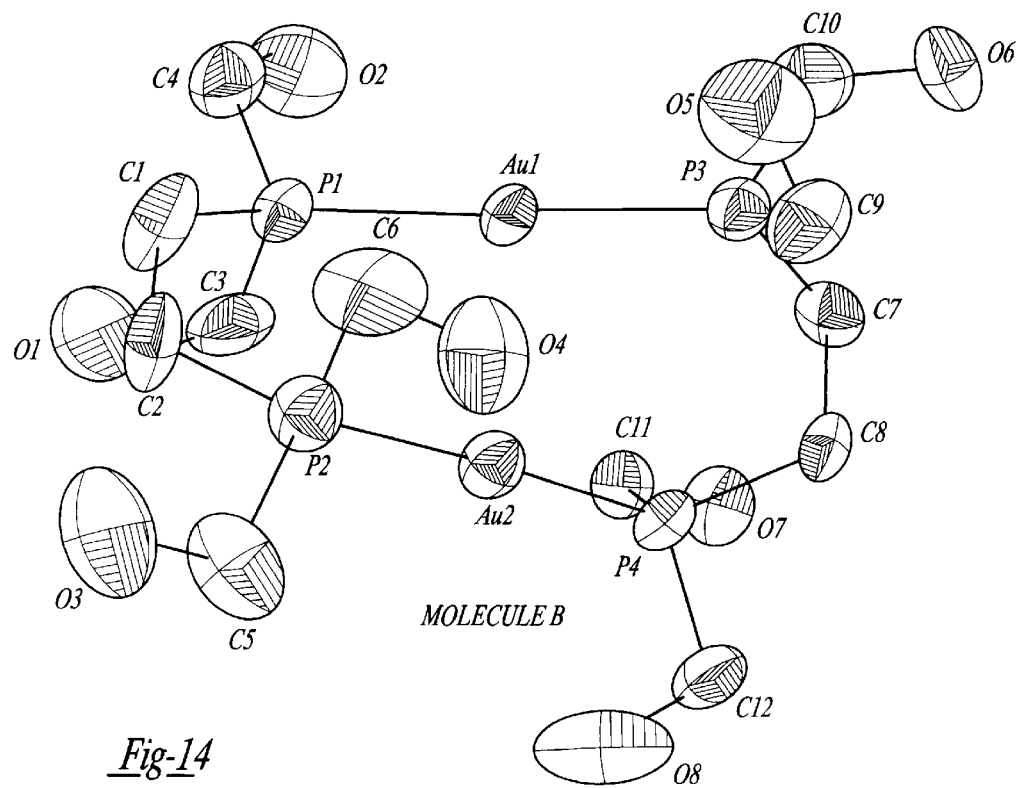
Fig-14

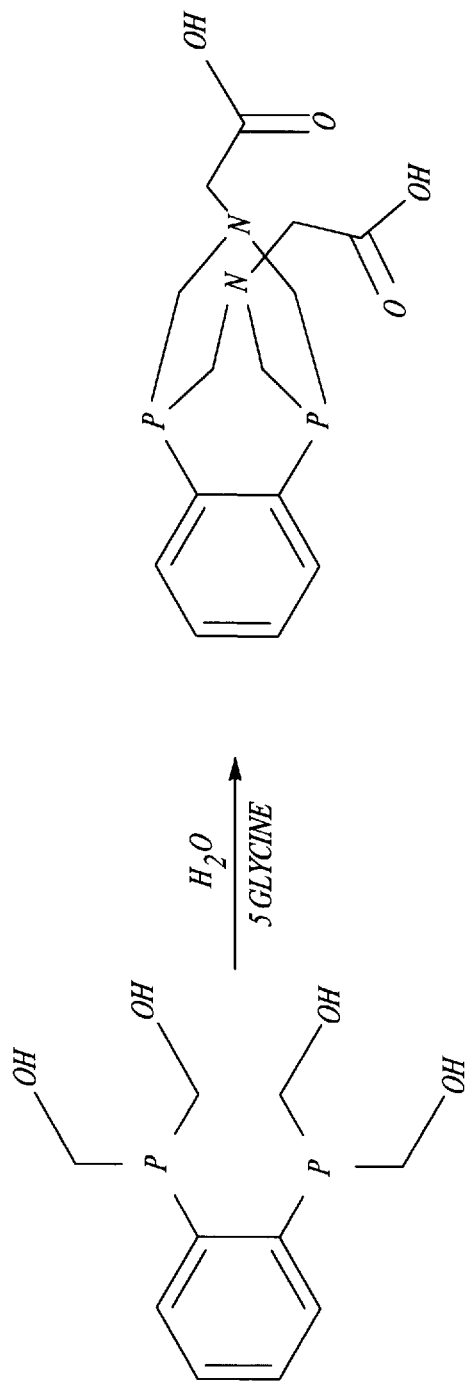
Fig-18  REACTION OF HMPB WITH GLYCINE

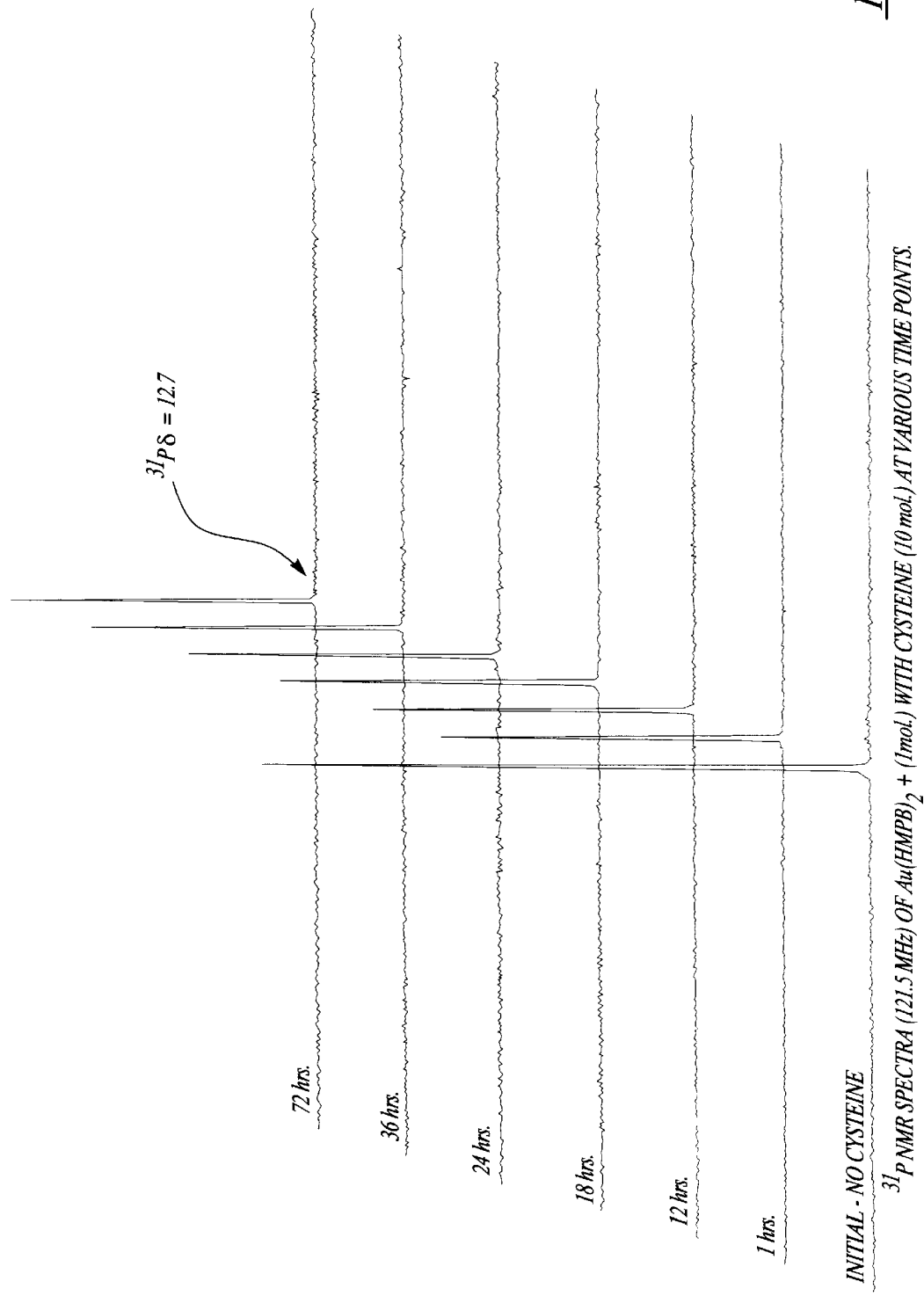

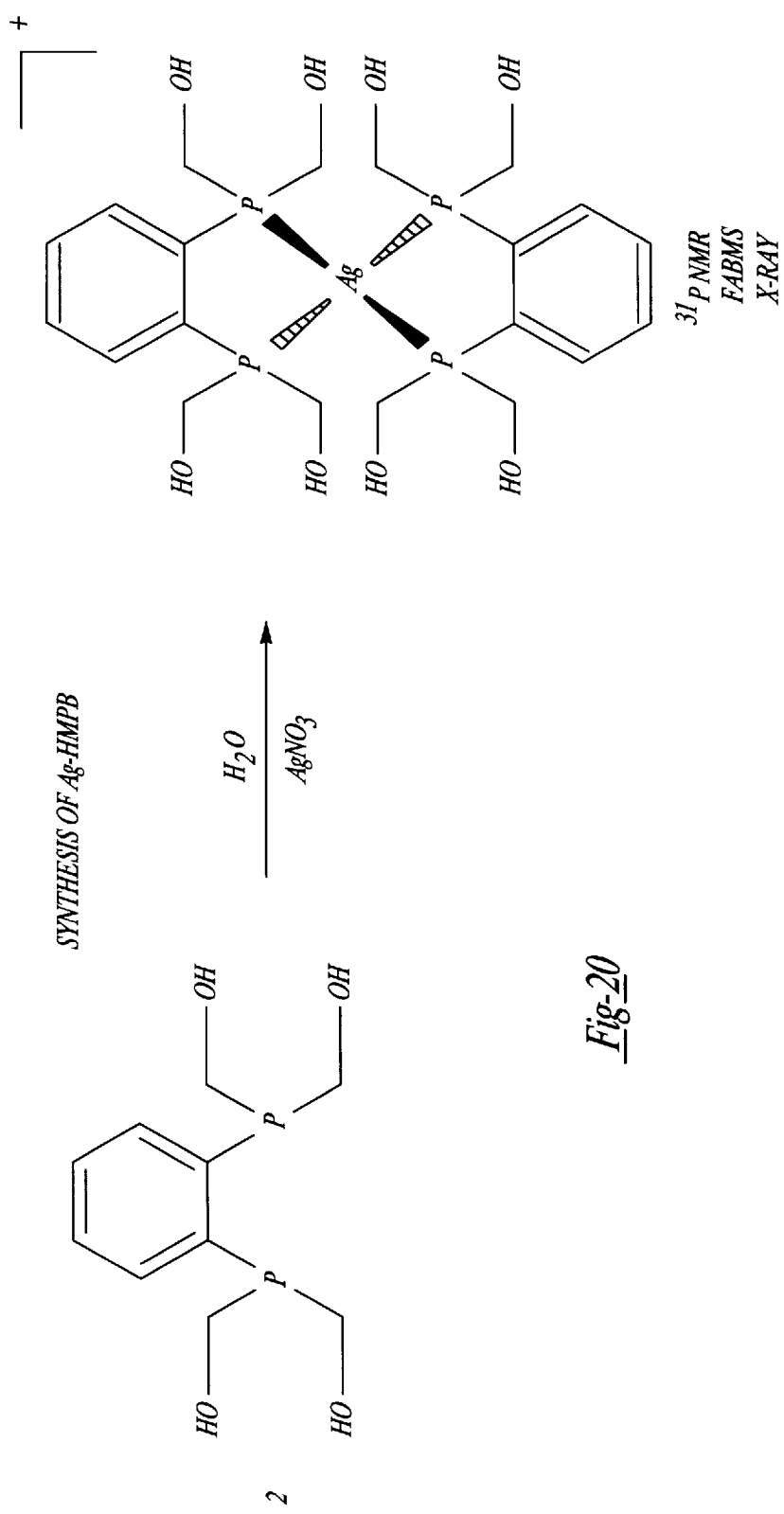

HYDROXYALKYL PHOSPHINE GOLD COMPLEXES FOR USE AS DIAGNOSTIC AND THERAPEUTIC PHARMACEUTICALS AND METHOD OF MAKING SAME

GRANT REFERENCE

The research carried out in connection with this invention was supported in part by a grant from the United States Department of Energy DOE-DE-FG02-89ER60875. The Government has certain rights in the inventions.

TECHNICAL FIELD

The present invention relates to pharmaceutical, especially radiopharmaceuticals, for use as diagnostic and therapeutic agents. More specifically, the present invention relates to a complex and method of synthesizing a complex which includes a ligand which complexes with a gold atom, typically a radionuclide, for use as diagnostic and/or therapeutic radiopharmaceuticals.

BACKGROUND OF THE INVENTION

Considerable research has focused on the development of water-soluble gold-containing complexes because of their potential in chemotherapeutic applications. For example, auranofin [(2,3,4,6-tetra-O-acetyl-1-thio-β-D-glucopyranosato-S)(triethylphosphine)]-gold(I) has been shown to be effective for the treatment of rheumatoid arthritis (Fricker, 1996; Berglof et al., 1978). Studies have demonstrated that this agent is superior to the traditional chrysotherapeutic drugs. Auranofin and related gold(I) compounds have been found to be active against interperitoneal P388 leukemia and are also cytotoxic to specific tumor cells (Simon et al., 1981; Mirabelli et al., 1985).

Compounds of gold that contain gold-198/199 isotopes are important in the development of radiopharmaceuticals for use in nuclear medicine. Gold-199 has a half-life of 3.2 days and decays with a beta emission of 0.46 MeV and a ganma emission of 0.158 MeV. Labeling of specific biomolecular vectors (e.g.; peptides or proteins) with gold-199 has been implicated as an important basis in the design of tumor specific radiopharmaceuticals for use in the diagnosis and therapy of human cancer (Volkert et al., 1991; Schubiger et al., 1996).

Despite significant medical applications of gold-containing compounds, the development of specific ligand systems to produce water-soluble, kinetically inert, and in vivo-stable complexes of gold with optimum toxicities in still in infancy (Shi et al., 1996; Rush et al., 1987). In this context, applicants explored the utility of 1,2-bis(bis (hydroxymethyl)phosphino)benzene (HMPB) and 1,2-bis (bis(hydroxymethyl)phosphino)ethane (HMPE) as complexing agents toward obtaining gold precursors.

Recent studies conducted by applicants have shown that the above mentioned hydroxymethyl phosphines produce water-soluble and kinetically inert complexes with several transition metal precursors that include rhenium, palladium and platinum (Reddy et al., 1996a; Reddy et al., 1996b). Additional studies performed by applicants have also demonstrated that this new generation of phosphines produce complexes with technetium-99m that are not only highly stable in vivo but also clear a body, primarily, via the kidneys as undecomposed complexes (Beming et al., 1996; Berning et al., unpublished results.

Applicants have formed novel water-soluble mono and dinuclear gold(I) complexes derived from the hydroxymethyl phosphine frameworks discussed above. X-ray crystallographic investigations to confirm the molecular constitutions of the mononuclear complex [Au{(HOH$_2$C)$_2$PC$_6$H$_4$P(CH$_2$OH)$_2$}$_2$]$^+$ and the dinuclear complex [Au$_2$ {(HOH$_2$C)$_2$PCH$_2$CH$_2$P(CH$_2$OH)$_2$}$_2$]$^{2+}$. These complexes represent examples of gold complexes suitable for use as radiopharmaceuticals and pharmaceutical which were previously unavailable.

Gold 198 and Gold-199 ($^{198/199}$Au) possess radionuclidic properties that make them attractive for use in formulating therapeutic radiopharmaceuticals. While $^{198}$Au is produced in reactors in relatively low specific activities, $^{199}$Au can be produced as a no-carrier added (NCA) reactant. $^{199}$Au is well suited for development of new radiopharmaceuticals via labeling of specific biomolecular vectors (such as peptides and proteins) to produce high specific activity, site-specific drugs. Therefore, it would be desirable to develop appropriate ligands that will produce complexes of gold metal with good in vivo and in vitro stabilities which is essential to the design of $^{198/199}$Au labeled radiopharmaceuticals.

Applicants have developed a new generation of water-soluble gold complexes. Systematic variation in the backbone of the ligand frameworks afford gold complexes possessing varying physico-chemical properties. High kinetic-stability makes this class of Au(I) complexes resistant to reduction under physiological pH conditions. This suggests that the utility of similar (or appropriately modified) ligands for the development of $^{198/199}$Au-labeled radiopharmaceuticals. These types of complexes can also be used to form stable Au(I) complexes (i.e., using macroscopic levels of non-radioactive gold) that are water-soluble for use in producing new drugs for other biomedical applications, including anti-arthritis drugs.

SUMMARY OF THE INVENTION

In accordance with the present invention, a complex and method for making same for use as a diagnostic or therapeutic pharmaceutical includes a ligand comprising at least one hydroxyalkyl phosphine donor group bound to a gold atom to form a gold-ligand complex that is stable in aqueous solutions containing oxygen, serum and other body fluids.

The present invention further provides a method of making a mono-dentate variant of the complex for use as a diagnostic and/or therapeutic pharmaceutical, the method including the following reactions

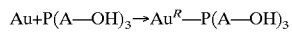

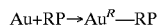

where in Au$^R$ is a gold atom in a reduced oxidation state as compared to Au; RP is a non-labeled radiopharmaceutical precursor containing a chelating moiety for chelating the reduced forms of the gold; and A is an alkyl group The present invention further provides a method of making a multi-dentate variant of the complex for use as a diagnostic and/or therapeutic pharmaceutical, the method including the following reactions

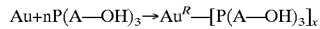

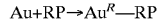

wherein Au$^R$ is a gold atom in a reduced oxidation state as compared to Au; X and n=1–6; RP is a non-labeled radiopharmaceutical precursor containing a chelating moiety for chelating the reduced forms of the gold; and A is an alkyl group.

The present invention further provides a method of treating a subject by administering an effective amount of a complex comprising a ligand comprising at least one hydroxyalkyl phosphine group bound to a gold atom to form a gold-ligand complex.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 illustrates a synthesis scheme for the synthesis of tris hydroxymethyl phosphine ligands;

FIG. 2 illustrates a synthesis scheme for the synthesis of hydroxymethyl phosphine benzene [HMPB] ligands according to the present invention;

FIG. 3 illustrates a synthesis scheme for the synthesis of monodentate phosphine gold complexes;

FIG. 14a–b are ORTEP drawings of $[Au_2\{(HOH_2C)_2PCH_2CH_2P(CH_2OH)_2\}_2]^{2+}$ 50% probability ellipsoids two crystallographically independent molecules (a) molecule A and (b) molecule B in the asymmetric unit.

FIG. 18 illustrates a reaction scheme for the reaction of HMPB with glycine;

FIG. 19 is a graph illustrating the $^{31}$P NMR spectra analysis of Au $(HMPB)_2^+$ with cysteine at various time points; and FIG. 20 illustrates the synthesis of Ag-HMPB.

DETAILED DESCRIPTION OF THE INVENTION

Figure 4:
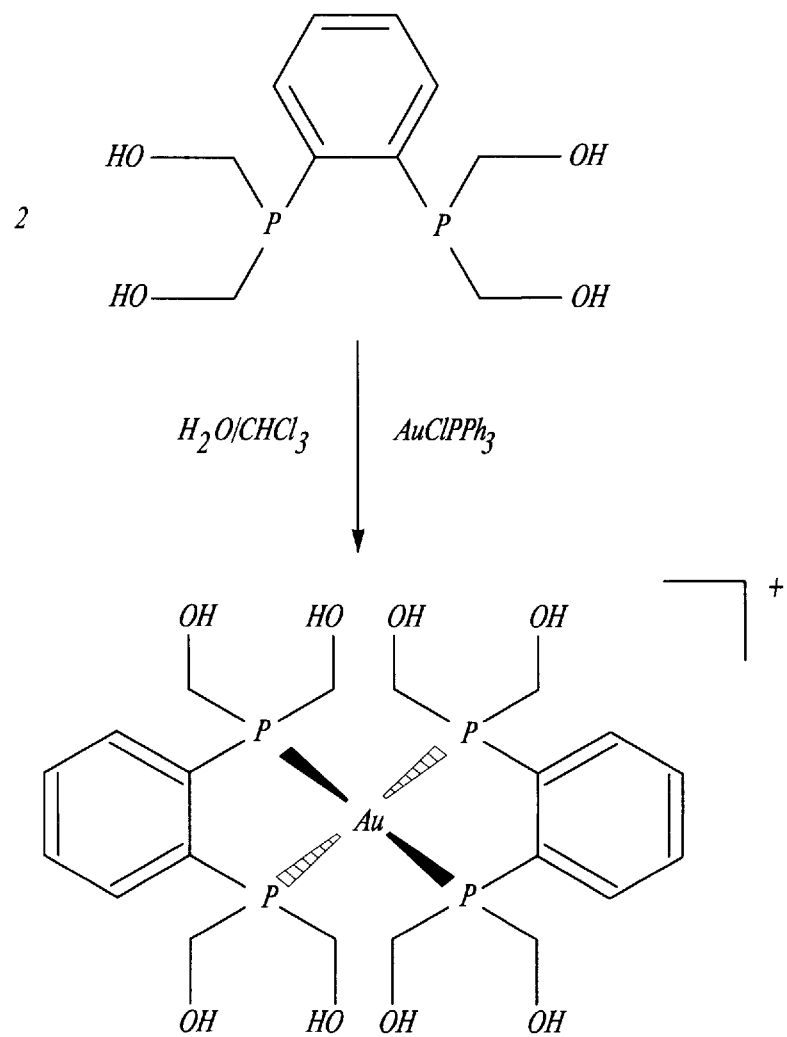
FIG. 4 illustrates a synthesis scheme for the synthesis of Au-HMPB complexes.

Generally, the present invention provides a complex for use as a diagnostic or therapeutic pharmaceutical. The complex includes a ligand including at least one hydroxyalkyl phosphine donor group bound to a gold atom to form a gold-ligand complex that is stable in aqueous solutions containing oxygen, serum and other body fluids. That is, the invention provides a ligand system containing at least one hydroxyalkyl phosphine donor group for use in forming complexes with gold metals wherein the complexes have high in vitro and/or in vivo stability. The gold atom can be an isotope selected from the group including γ and β emitting isotopes.

The phosphorous ligands were chosen since the phosphorous atom provides a plethora of electron density that promotes formation of highly stable ligand-metal bonds. This can occur even with the gold metal in its higher oxidation states.

The hydroxyalkyl phosphine ligand is complexed with the gold metal, generally from the group including $^{198}$Au and $^{199}$Au isotopes. These complexes contain a ratio of ligand to gold that is greater than or equal to 1:1 which makes the resulting chelates small and well-defined These specific combinations permit the formation of the complexes in a one step, high yield reaction as described below, especially for use with readily available chemical forms of gold radionuclides. Other metals suitable for being chelated include silver (Ag) as shown in FIG. 20.

For example, $AuCl_4^-$ chelates can be used. It has been determined that this type of gold containing compound forms highly stable chelates with a variety of hydroxyalkyl phosphine ligands to yield new complexes having therapeutic and/or diagnostic uses A complex according to the present invention can include a complex of the formula

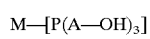

wherein M is gold metal in a reduced oxidation state, n is 1–6, and A is an alkyl group. In a preferred embodiment of the present invention, A is —$CH_2$—. Additionally, A can include —$C_2H_4$— and iso- or normal-$C_3H_6$—.

The gold-ligand complexes can include other donor atoms or groups on the same ligand as the donor hydroxyalkyl phosphine group. These other donor groups can include N, S, O, or P atoms for coordinating the gold atom. In addition, the donor groups can further include amines, amides, thiols, carboxyls, and hydroxyls for coordinating the gold atom.

In another preferred embodiment of the present invention, the complexes can include a bidentate ligand of the formula $$(HOA)_2P-X-P(AOH)_2$$

wherein A is —$CH_2$—, —$C_2H_4$—, or iso- or normal-$C_3H_6$—, and X is —$(CH_2)_n$— where n=1–4, —$CH_2CHR$—, —$CH_2CHRCH_2$—, —$CHRCH_2CH_2$—, or R'-aromatic where R' is H, an alkyl group of $C_1$–$C_4$, an aromatic group, —OH, —SH, —$NH_2$, —COOH, activated esters, N-hydroxysuccinimides, benzyl isothiocyanate, alkyl halides, or cyclohexyldiimide. Specific examples of bidentate ligands used to complex with gold can include 1,2-bis (bis(hydroxymethyl)phosphino)benzene (HMPB, 1) and 1,2-bis(bis(hydroxymethyl)phosphino)ethane (HMPE, 2) as set forth below. As set forth in Scheme 1 of FIG. 11, the formation of gold complexes according to the present invention with the ligands HMPB and HMPE are shown.

In further preferred embodiments, complexes according to the present invention are contemplated which include multidentate ligands of the formula $$[(HOA)_2PI]_2-P-X-P[YP(AOH)_2]_2$$

wherein A is —$CH_2$—, —$C_2H_4$—, or iso- or normal-$C_3H_6$—, and X is —$(CH_2)_n$— where n=1–4, —$CH_2CHR$—, —$CH_2CHRCH_2$—, —$CHRCH_2CH_2$—, or R'-aromatic where R' is H, an alkyl group of $C_1$–$C_4$, an aromatic group, —OH, —SH, —$NH_2$, —COOH, activated esters, N-hydroxysuccinimides, benzyl isothiocyanate, alkyl halides, or cyclohexyldiimide, and Y is $CH_2$—, —$C_2H_4$— or —$C_3H_6$—. Along the lines of this embodiment, further embodiments can exist wherein all of the donor atoms can be phosphorous atoms. Additionally, embodiments are contemplated wherein at least one donor group is a hydroxyalkyl phosphine group.

Furthermore, complexes according to the present invention are contemplated wherein two donor atoms are hydroxyalkyl phosphine phosphorous-atoms and two donor atoms are atoms other than phosphorous-atoms. These complexes have the general formula $$[(HOA)_2PY]_2K-X-K]YP(AOH)_2]_2$$

wherein A is —$CH_2$—, —$(CH_2)_2$—, or iso- or normal-$C_3H_6$—, K includes donor atoms or groups selected from the group consisting of —N—, —$N(R)^+$—, —N(H)—, Ag, and —S—, Y is —$CH_2$—, —$(CH_2)_2$—, or iso- or normal-$C_3H_6$ X is —$CH_2$—, —$(CH_2)_2$—, —$(CH_2)_3$—, —$(CH_2)_4$—, —$CH_2CHR$—, —$CH_2CHRCH_2$—, —$CHRCH_2CH_2$—, or R'- aromatic where R' and R can be the same or different and are selected from H, —OH, —SH, —$NH_2$, —COOH, activated esters, N-hydroxysuccinimides, benzyl isothiocyanate, alkyl halides, and cyclohexyldiimide.

A variant of this embodiment can include a complex wherein two donor atoms are hydroxyalkyl phosphine phosphorous-atoms and two donor atoms are nitrogen-atoms (P2N2). These complexes can have the general formula $$E=C-NR-[X-P(AOH)_2]_2$$

wherein X is —$CH_2$—, —$(CH_2)_2$—, —$C_3H_6$—, A is —$CH_2$—, —$(CH_2)_2$—, —$C_3H_6$—, E is O or S, R can be the same or different and is selected from H, —OH, —SH, —$NH_2$, —COOH, activated esters, N-hydroxysuccinimides, benzyl isothiocyanate, alkyl halides, or cyclohexyl diimide, N is nitrogen, and Y is —$CH_2$—, —$(CH_2)_2$—, or iso- or normal-$C_3H_6$—.

An additional embodiment is contemplated wherein two donor atoms are hydroxyalkyl phosphine phosphorous-atoms and two donor atoms are sulfur-atoms (P2S2).

Complexes contemplated under this embodiment have the general formula $$E=C-SR-[X-P)AOH)_2]_2$$

wherein X is —$CH_2$—, —$(CH_2)_2$—, —$C_3H_6$—, A is —$CH_2$—, —$(CH_2)_2$—, —$C_3H_6$—, E is O or S, R can be the same or different and is selected from H, —OH, —SH, —$NH_2$, —COOH, activated esters, N-hydroxysuccinimides, benzyl isothiocyanate, alkyl halides, or cyclohexyldiimide, S is sulfur, and Y is —$CH_2$—, —$(CH_2)_2$—, or iso- or normal-$C_3H_6$—.

Figure 16:
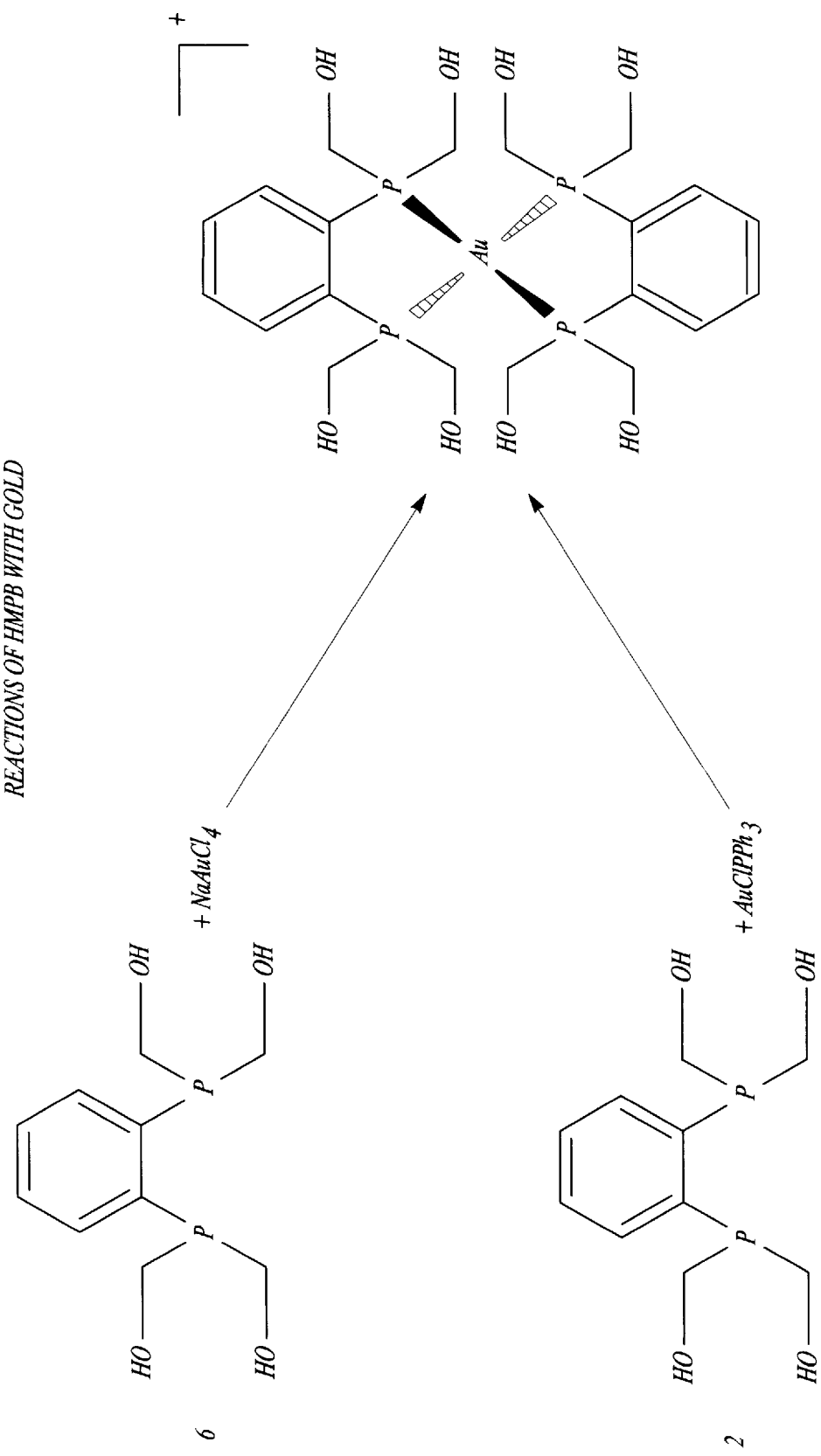
FIG. 16 illustrates two reaction pathways for the reaction of HMPB with gold.
Figure 17:
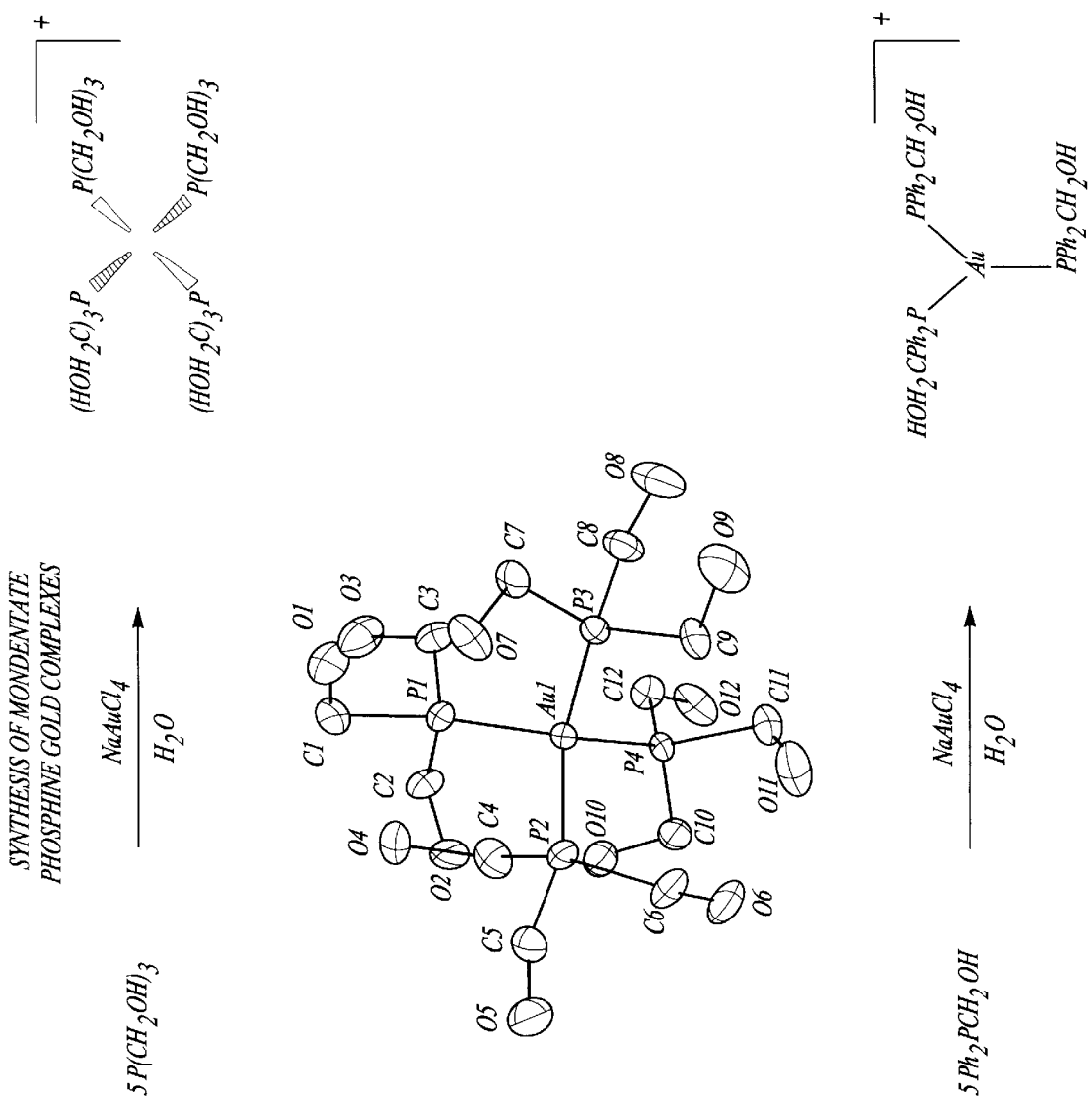
FIG. 17 illustrates a synthesis scheme for the synthesis of monodentate phosphine gold complexes in accordance with the present invention.

Complexes made in accordance with the present invention for use as diagnostic and/or therapeutic pharmaceuticals can be made by the following general reactions:

$$Au + RP \rightarrow Au^R - RP$$

$$Au + P(A-OH)_3 \rightarrow Au^R - P(A-OH)_3$$

wherein $Ar^R$ is a gold atom in a reduced oxidation state as compared to Au, RP is a non-labeled radiopharmaceutical precursor containing a chelating moiety for chelating the reduced forms of the gold, and A is an alkyl group as is shown in FIGS. 16 and 17. The chelating moiety, in general, is a hydroxyalkyl phosphine ligand as described herein.

In a preferred embodiment of the present invention, the alkyl group is methyl but can include —$C_2H_4$—, an iso-or normal-$C_3H_6$. The gold atom can be any gold atom including isotopes selected from γ and β emitting isotopes, such as $^{198}$Au and $^{199}$Au.

Additionally, the method can include the step of conjugating a biomolecule or other free amine containing molecule, such as a monoclonal antibody, protein, toxin, dye, amino acid, or other biomolecules known to those skilled in the art, to the complex. Preferably, the conjugation of the biomolecule and ligand is accomplished by reacting a hydroxymethyl phosphine group of an amine-free first molecule (ligand) with at least one free amine group of a second molecule (the biomolecule) to covalently bond the first molecule with the second molecule through an aminomethyl phosphorus linkage as generally shown in FIG. 18. Specifically, the formation includes the reaction of an HMP group(s) (R—$P(CH_2OH)$) with primary and/or secondary amines over a wide pH range to form well-defined conjugate products in which a specific molecule is covalently linked to a different molecule or solid surface. To fully exploit this reaction, it is essential that the compounds or cross-linking reagents containing appended HMP group(s) be synthesized ($RP(CH_2OH)_2$, where R≠$CH_2OH$ and is any other organic molecule or group that can be specifically conjugated to another molecule via the reaction of the HMP group with a primary or secondary amine) on the material or compound to be conjugated.

In a preferred reaction scheme, the HMP groups are separated by two carbon atoms. These fully characterized molecules can, in turn, be used to conjugate or cross-link one molecule containing an HMP group to another molecule or material that has a primary and/or secondary amine group (s) located at a specific site or sites on the molecule.

Additionally, the conjugation reactions can involve reactive groups such as benzyl isothiocyanate, bromoacetamide, activated esters, N-hydroxysuccinimides, cleavable ester linkages, and aldehydes. Accordingly, a single monoclonal antibody or several monoclonal antibodies can be added to the gold-ligand complex to provide specificity of the binding of the ligand metal complex to specific surface antigen or target tissue.

Complexes containing multidentate ligand-gold complexes according to the present invention can be made by the following general reactions:

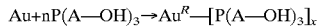

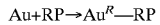

wherein $Au^R$ is a gold atom in a reduced oxidation state as compared to Au, x and n=1–6, RP is a non-labeled radiopharmaceutical precursor containing a chelating moiety for chelating the reduced forms of the gold, and A is an alkyl group.

Preferably, the alkyl group is methyl, however, the alkyl group can include $C_2H_4$, and iso- or normal-$C_3H_6$. The gold atom can be selected from any gold complex including γ and/or β emitting isotopes, such as $^{198}Au$ and $^{199}Au$. Additionally, the method can include the step of conjugating a biomolecule to the complex as set forth above.

The present invention also teaches a method for treating a subject with a condition such as arthritis which includes administering a therapeutically effective amount of a complex according to the present invention.

A "therapeutically effective amount" is an amount of a complex of the present invention that when administered to a patient ameliorates a symptom of the specific disease or condition being treated. If therapeutically effective amount of a complex of the present invention can easily be determined by one skilled in the art by administering a quantity of a complex to a patient and observing the result. In addition, those skilled in the art are familiar with identifying patients having the particular disease or condition and are readily able to identify patients who suffer from these diseases or conditions.

The complexes of the present invention can be administered to a patient alone or as part of a composition that contains other components such as excipients, diluents, and carriers, all of which are well-known in the art. The compositions can be administered to humans and animals either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active complex is admixed with at least one customary inert excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose and acacia; (c) humectants, as for example, glycerol; (d) disintegrating agents, as for example, agar—agar, calcium carbonate, potato or tapioca starch, alginic acid, certain complex silicates and sodium carbonate; (e) solution retarders, as for example paraffin; (f) absorption accelerators, as for example, quaternary ammonium complexes; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills, and granules can be prepared with coatings and shells, such as enteric coatings and others well-known in the art. They may contain opacifying agents and can also be of such composition that they release the active complex or complexes in a certain part of the intestinal tract in a delayed manner. Examples of embedding compositions which can be used are polymeric substances and waxes. The active complexes can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active complexes, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active complexes, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the complexes of the present invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a complex of this invention include ointments, powders, sprays, and inhalants. The active component is admixed under sterile conditions with a physiologically acceptable carrier and any preservative, buffers, or propellants as may be required. Ophthalmic formulations, eye ointments, powders, and solutions are also contemplated as being within the scope of this invention.

The complexes and/or compositions of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is sufficient. The specific dosage used, however, can vary. For example, the dosage can depend on a numbers of factors including the requirements of the patent, the severity of the condition being treated, and the pharmacological activity of the complex being used. The determination of optimum dosages for a particular patient is well-known to those skilled in the art.

In addition, the complexes of the present invention can exist in unsolvated as well as solvated forms with pharmaceutically acceptable solvents such as water, ethanol, and the like. In general, the solvated forms are considered equivalent to the unsolvated forms for the purposes of the present invention.

Methods

I. Development of Ligands

The ligands used in the synthesis of water-soluble gold complexes are depicted in Schemes 1 and 2 of FIGS. 1 and 2 respectively. Examples of modifications of the prototypes shown in Schemes 1 and 2 are possible and that can afford functionalized ligand frameworks that can be attached to Au-199 labeled complexes to other molecules (e.g., biomolecules such as monoclonal antibodies).

II. Development of Water-soluble Gold Complexes

Figure 5:
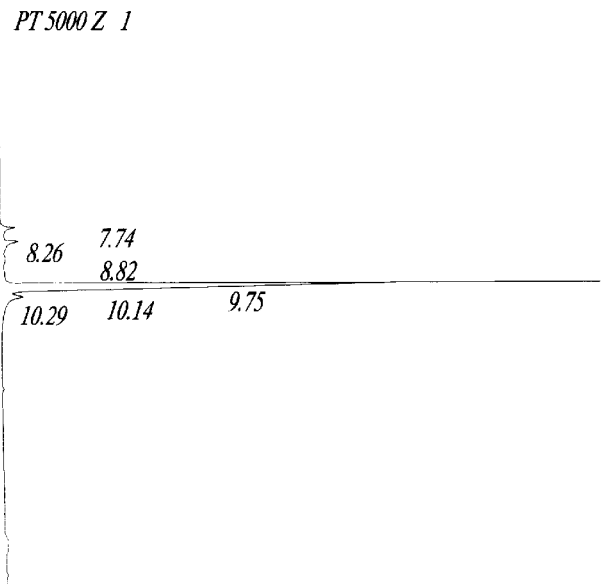
FIG. 5 is a graph illustrating an HPLC analysis of a gold-HMPB complex.
Figure 6:
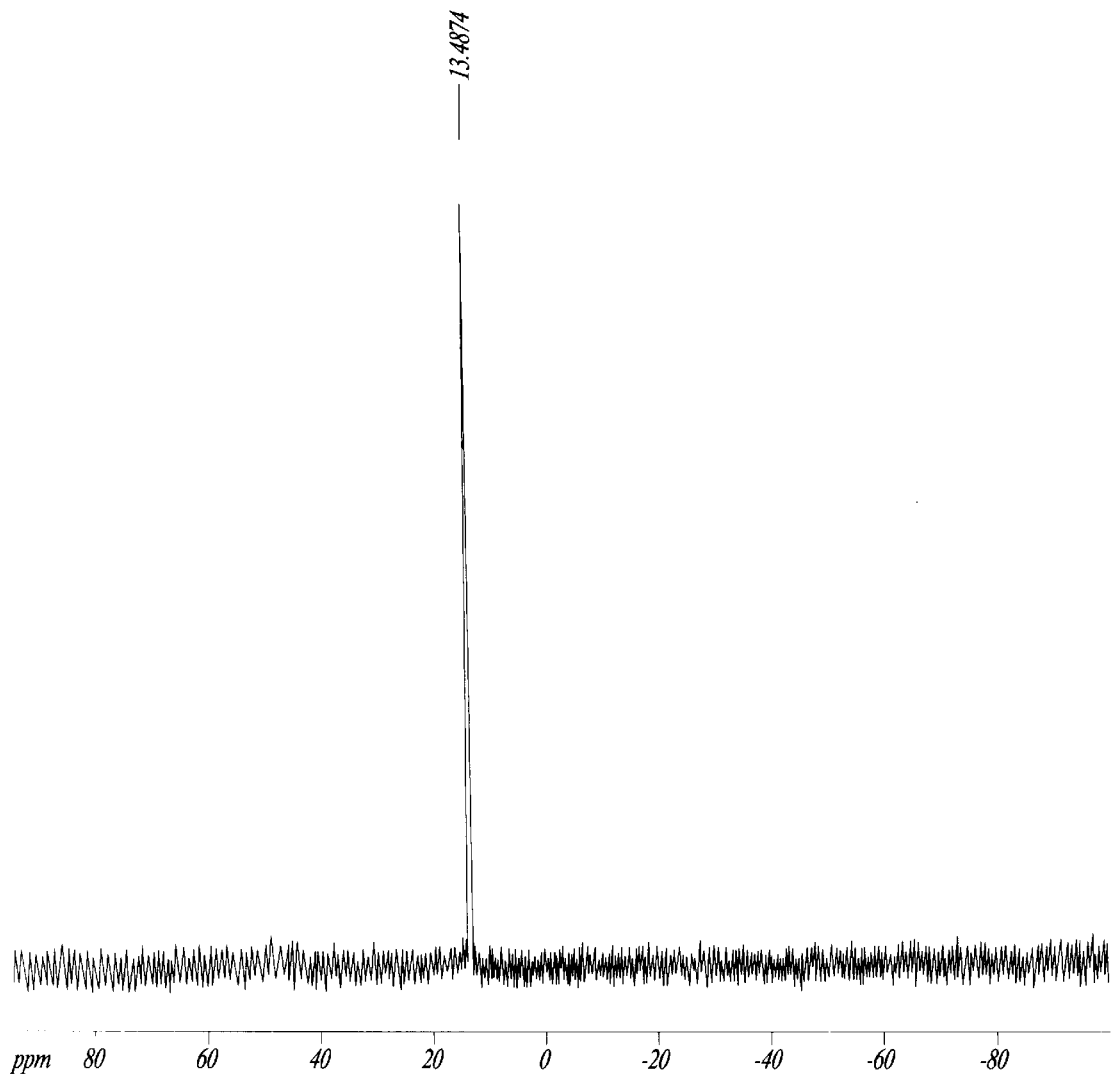
FIG. 6 is a graph illustrating a NMR spectra analysis of a Au-HMPB complex wherein a large excess of cysteine was added at the initial time point where the cysteine to illustrate that the complexes according to the present invention are kinetically inert in solutions that contain a large excess of cysteine.
Figure 7:
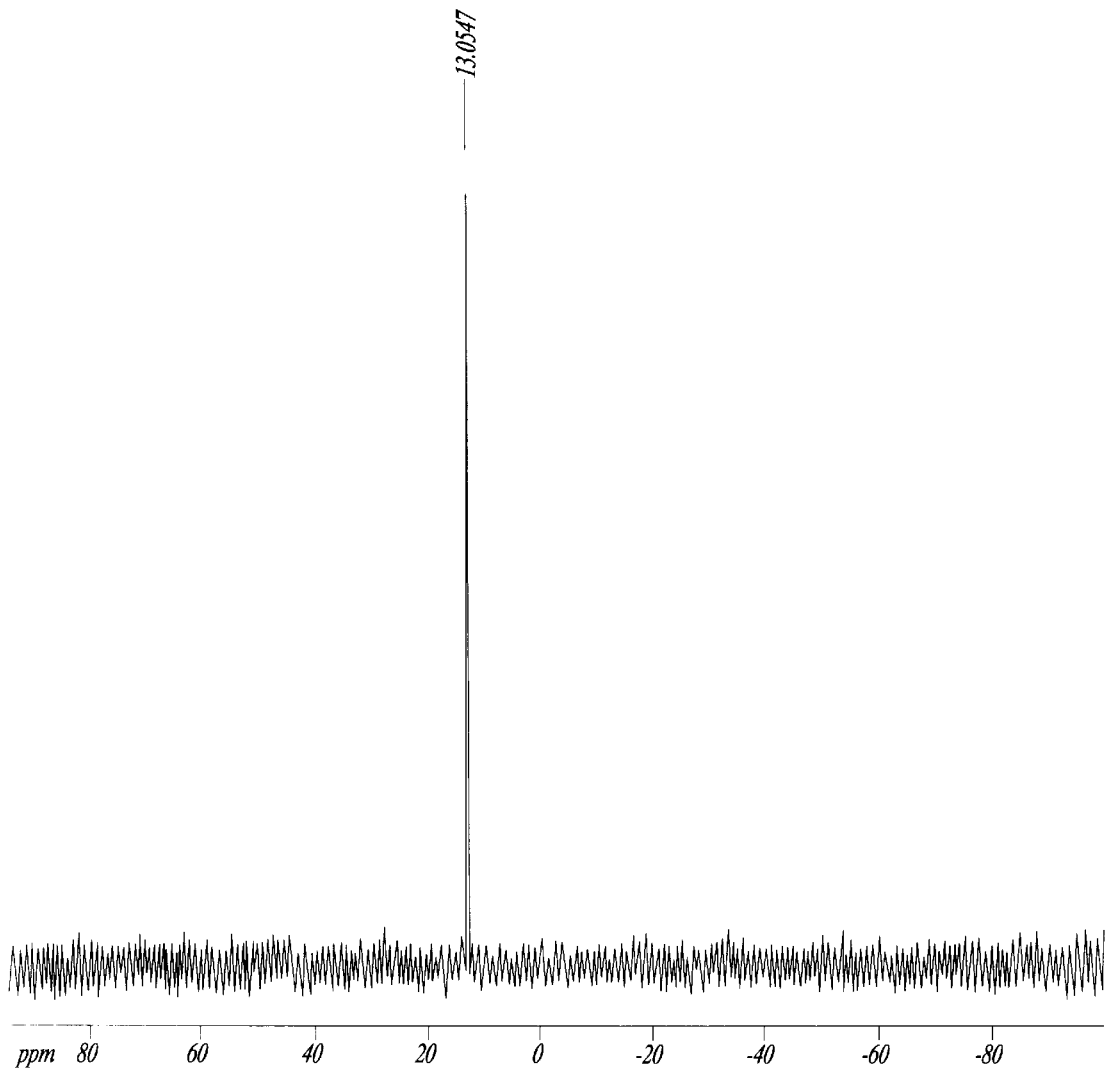
FIG. 7 is a graph illustrating a NMR spectra analysis of a Au-HMPB complex wherein a large excess of cysteine was added to illustrate that the complexes according to the present invention are kinetically inert in solutions that contain a large excess of cysteine, wherein the graph illustrates a point fifteen minutes following the addition of the cysteine.
Figure 8:
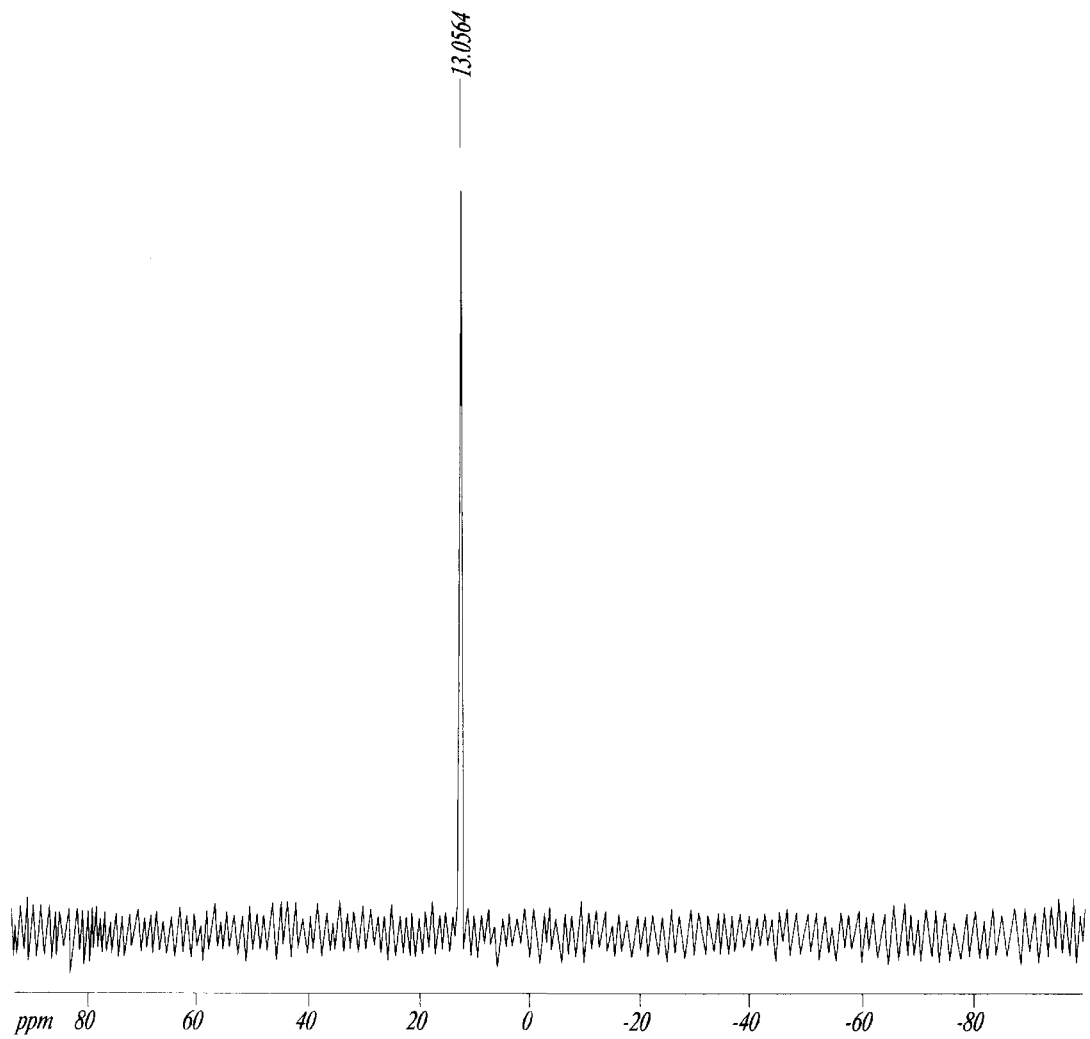
FIG. 8 is a graph illustrating a NMR spectra analysis of a Au-HMPB complex wherein a large excess of cysteine was added to illustrate that the complexes according to the present invention are kinetically inert in solutions that contain a large excess of cysteine, wherein the graph illustrates a point eighteen hours following the addition of the cysteine.
Figure 9:
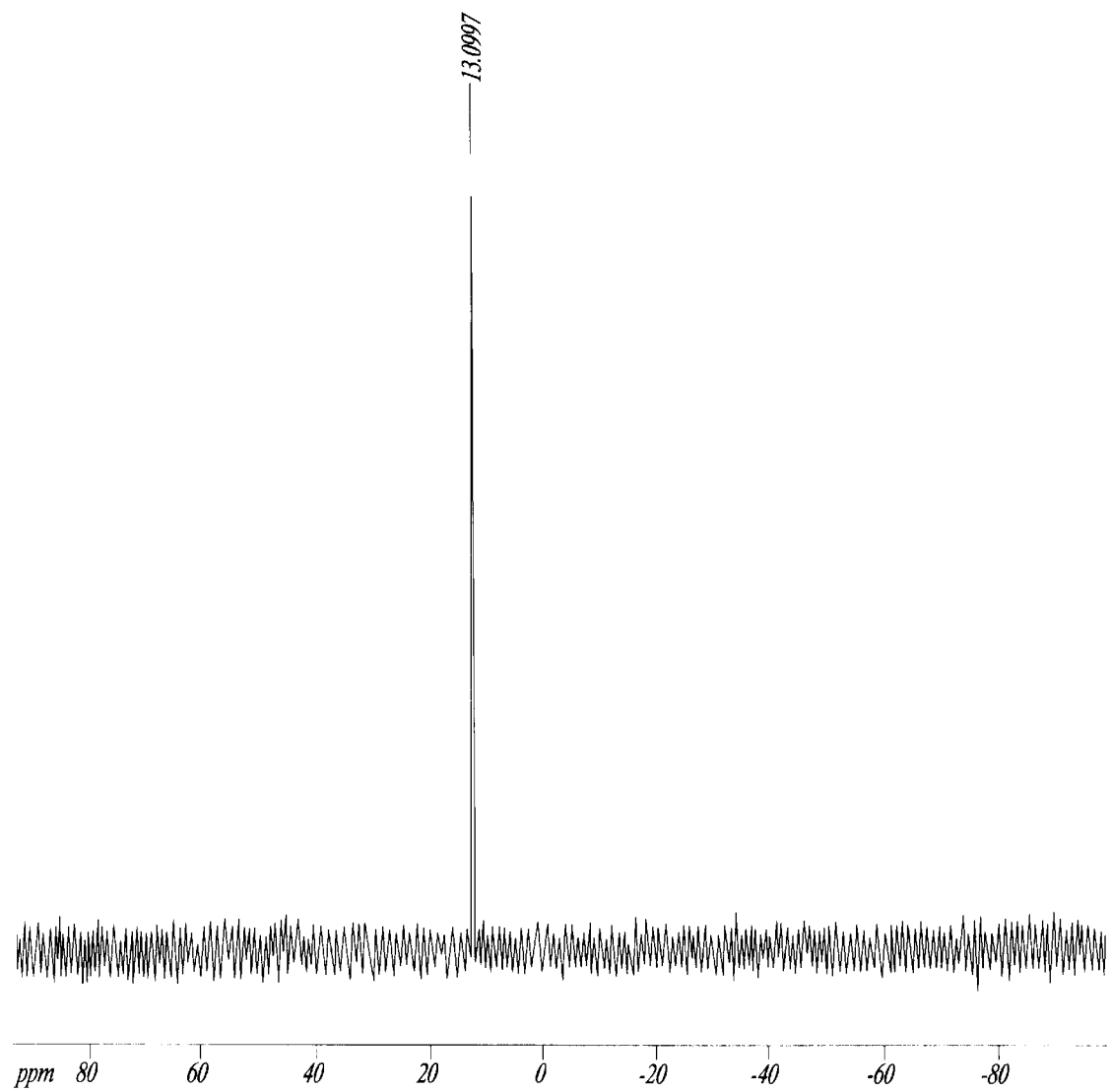
FIG. 9 is a graph illustrating a NMR spectra analysis of a Au-HMPB complex wherein a large excess of cysteine was added to illustrate that the complexes according to the present invention are kinetically inert in solutions that contain a large excess of cysteine, wherein the graph illustrates a point twenty-four hours following the addition of the cysteine.
Figure 10:
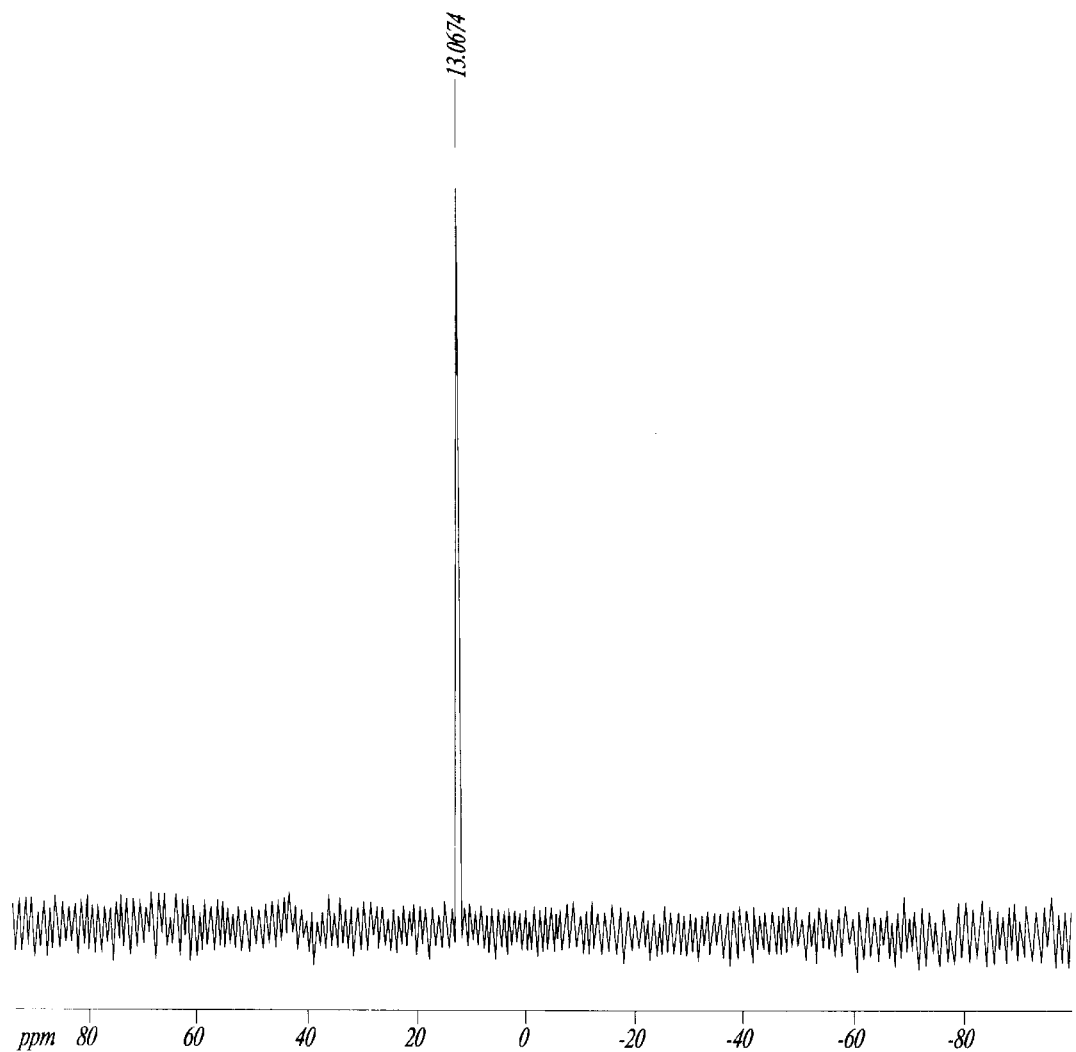
FIG. 10 is a graph illustrating a NMR spectra analysis of a Au-HMPB complex wherein a large excess of cysteine was added to illustrate that the complexes according to the present invention are kinetically inert in solutions that contain a large excess of cysteine, wherein the graph illustrates a point thirty-six hours following the addition of the cysteine.

The reactions summarized in Schemes 3 and 4 shown in FIGS. 3 and 4, respectively, illustrate the synthetic methods for the production of water-soluble Au(I) complexes are derived from mono-phosphines and bis phosphines. The Au(I) complexes of tri(hydroxymethyl)phosphine (THP) and hydroxymethyl phosphino benzene (HMPB) were formed as singular chemical species in near quantitative yields upon simple mixing of Au(III) or Au(I) precursors with aqueous solutions of ligands. The HPLC profile of the Au(I)-HMPB complex formed is shown in FIG. 5. The phosphorus-31 NMR data of Au(I) THP and Au(I) HMPB complexes suggest that these complexes are kinetically inert in water over extended periods of time (>72 h). Additional studies using $^{31}$P-NMR provide evidence that these complexes remained kinetically inert in solutions that contained a large excess of cysteine as shown in FIGS. 6–10. This result indicates that when Au(I) is complexed with hydroxymethylene phosphine (HMP) groups, Au(I) in the complex is resistant to reduction to gold metal in biological systems. Detailed spectroscopic ($^1$H and $^{31}$P NMR) and X-ray crystallographic investigations have confirmed the molecular constitutions of Au(I)-THP and Au(I)-HMPB complexes.

The ability of HMP ligands to form Au(I) complexes that have high kinetic stability in aqueous solutions provides new opportunities for producing a spectrum of Au(I) complexes for biomedical applications. For example, Au-199 has physical properties that make it an attractive radionuclide to formulate new site-directed therapeutic radiopharmaceuticals. A major problem encountered in labeling molecules for in vivo targeting with radioactive gold is to be able to bind well-defined $^{198/199}$Au complexes to biomolecules that are stable biological fluids (e.g., serum). Several attempts have been made to form Au-complexes with high stabilities, however, previous complexes proved susceptible to in vitro and/or in vivo dissociation which often involved reduction of Au(I) or Au(III) to gold metal. Results from applicant's studies indicate that the use of HMP based ligands will provide the means to overcome these stability/oxidative limitations.

The fact that mono- and bidentate HMP ligands form stable complexes with Au(I) is a strong indication that a variety of multidentate HMP ligands can be synthesized that will be effective in producing the corresponding Au(I) complexes with high aqueous stability. The results of these studies provide realistic prospects for production of Au-198 or Au-199 complexes for use in radiopharmaceutical applications. The ligand framework (as shown in Schemes 1 and 2 of FIGS. 1 and 2, respectively) can be modified so that these types of ligands can be used as bifunctional chelating agents (BFCAs) that will covalently link to the HMP ligands to other molecules (e.g., bio molecules) to design new radiopharmaceuticals. These BFCAs can be attached to other molecules, either prior to or following complexation with radioactive gold, to produce the radiolabeled drugs.

Experimental Section

All reactions were carried out under purified nitrogen by standard Schlenk techniques. Solvents were purified and dried by standard methods and distilled under nitrogen prior to use. NaAuCl$_4$ and AuClPPh$_3$ were purchased from Alfa and Strem Chemical Companies, respectively, and used without further purification. Cysteine was purchased from Sigma Chemical Co. and used without further purification. The synthesis of (HOH$_2$C)$_2$PC$_6$H$_4$P(CH$_2$OH)$_2$ (1) and (HOH$_2$C)$_2$PCH$_2$CH$_2$P(CH$_2$OH)$_2$ (2) (Reddy et al., 1996a) are reported earlier. Nuclear magnetic resonance spectra were recorded on a Bruker ARX-300 spectrometer using D$_2$O or CD$_3$OD as a solvent. The $^1$H NMR chemical shifts are reported in parts per million, downfield from external standard SiMe$_4$. The $^{31}$P NMR (121.5 MHz) spectra were recorded with 85% H$_3$PO$_4$ as an external standard, and positive chemical shifts lie downfield of the standard. Mass spectra were performed by Washington University, St. Louis, Mo.

Figure 11:
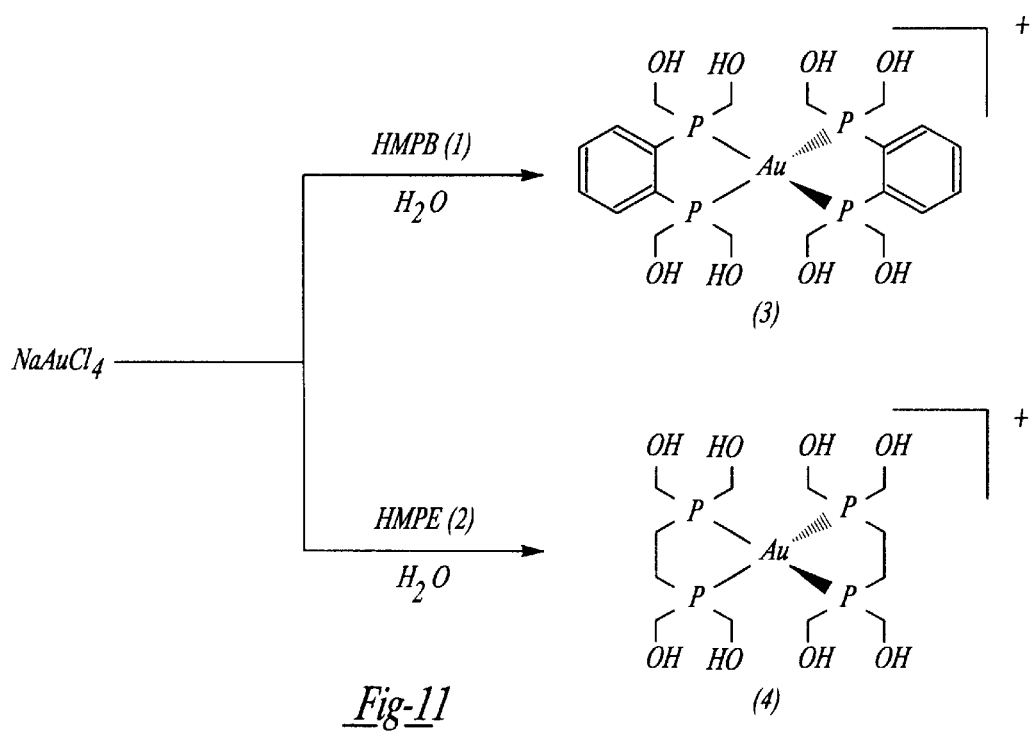
FIG. 11 illustrates a synthesis scheme for the preparation of complexes 3 and 4 from the reaction of $NaAuCl_4$ with either HMPB (1) or HMPE (2), respectively.

Synthesis of [Au {(HOH$_2$C)$_2$PC$_6$H$_4$P(CH$_2$OH)$_2$}$_2$]$^+$ (complex (3) of FIG. 11.

An aqueous solution (5 cm$^3$) of NaAuCl$_4$ (0.5 mmol.) was added dropwise to (HOH$_2$C)$_2$PC$_6$H$_4$P(CH$_2$OH)$_2$ (2.5 mmol.) also in water (5 cm$^3$) at 25° C. with constant stirring. The stirring was continued for two hours and the product was filtered off as a white solid in 90% yield. HRFAB/MS calculated for C$_{20}$H$_{32}$O$_8$P$_4$Au: 721.0713; Found: [M$^+$], m/z=721.0699. mp: 163°–165° C. (dec.). $^1$H NMR (CD3OD): δ 4.40, 4.23 (AB quartet), 16 H, $^2$J$_{HH}$=12.92 Hz, P(CH$_2$OH)$_2$), 7.64 (m, 4 H, C$_6$H$_4$), 8.12 (m, 4 H, C$_6$H$_4$). $^{13}$C NMR (CD$_3$OD): δ 62.4 (m, P(CH$_2$OH)$_2$). 132.4 (s, C$_6$H$_4$), 134.1 (s, C$_6$H$_4$), 141.4 (m, C$_6$H$_4$). $^{31}$P NMR (CD$_3$OD): δ 12.2(s).

Synthesis of [Au{(HOH$_2$C)$_2$PCH$_2$CH$_2$P(CH$_2$OH)$_2$}$_2$]$^+$ (complex (4) of FIG. 11.

An aqueous solution (5 cm$^3$) of NaAuCl$_4$ (0.5 mmol.) was added dropwise to (HOH$_2$C)$_2$PCH$_2$CH$_2$P(CH$_2$OH)$_2$ (2.5 mmol.) also in water (5 cm$^3$) at 25° C. with constant stirring. The stirring was continued for two hours and the sample was concentrated to 1 ml under reduced atmosphere and loaded onto a preconditioned Water's Sep-Pak Vac column. The column was eluted with water followed by methanol. Collection of the methanol fractions and removal of the solvent afforded the desired product in 85% yield. HRFAB/MS Calcd. for $C_{12}H_{32}O_8P_4Au$: 625.0713; Found [M$^+$], m/z= 625.0720. $^1$H NMR (D$_2$O): δ 4.00, 3.56 (AB quartet, 8 H, $^2J_{HH}$=13.53 Hz, P(CH$_2$OH)$_2$), 1.84 (s, 4 H, CH$_2$CH$_2$). $^{13}$C NMR (D$_2$O): δ 58.8 (m P(CH$_2$OH)$_2$), 19.0 (m. CH$_2$CH$_2$). $^{31}$P NMR (D$_2$O): δ 18.6(s).

Figure 12:
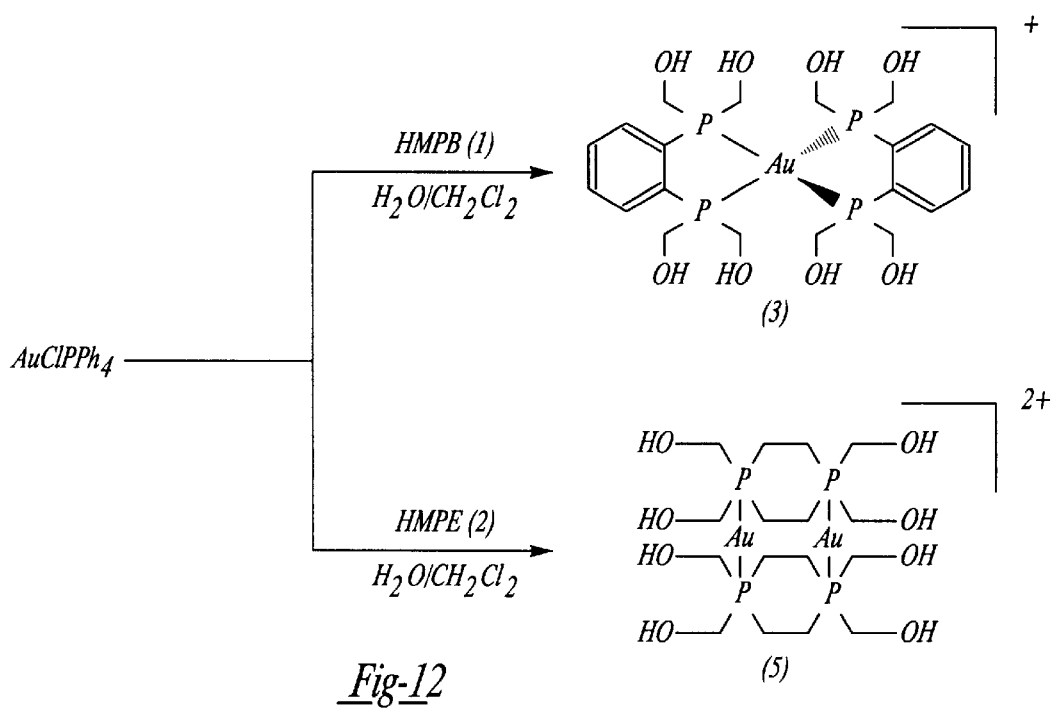
FIG. 12 illustrates a synthesis scheme for the formation of complexes in accordance with the present invention by reacting $AuClPPh_3$ with HMPB or HMPE to yield complexes 3 or 5, respectively.

Synthesis of [Au$_2${(HOH$_2$C)$_2$PCH$_2$CH$_2$P(CH$_2$OH)$_2$}$_2$]$^{2+}$ (complex (5) of FIG. 12.

AuClPPh$_3$ (4.0 mmol.) in dichloromethane (5 cm$^3$) was added to (HOH$_2$C)$_2$PCH$_2$CH$_2$P(CH$_2$OH)$_2$ (2.0 mmol.) in water (5 cm$^3$) at 25° C. under constant stirring. The stirring was continued for three hours upon which the aqueous layer was separated and concentrated under reduced pressure. HRFAB/MS Calcd. for $C_{12}H_{32}O_8P_4Au_2$Cl: 857.0066. Found [M$^+$], m/z=857.0062. mp: 153°–156° C. 1 H(D$^2$O): δ 4.40 (s, 16 H, PCH$_2$OH), 2.48 (br s, 8H, PCH$_2$CH$_2$P). $^{13}$C (D$_2$O): δ 56.4 (br s, PCH$_2$OH), 14.3 (br s, PCH$_2$CH$_2$P). $^{31}$P(D$_2$O): δ 36.9 (s).

Cysteine Challenge Study for [Au{(HOH$_2$C)$_2$PC$_6$H$_4$P(CH$_2$OH)$_2$}$_2$]$^+$.

Cysteine (2.2 mmol.) in a water/methanol mixture (75/25, 5 cm$^3$) was added to [Au{(HOH$_2$C)$_2$PC$_6$H$_4$P(CH$_2$OH)$_2$}$_2$]$^+$ (0.2 mmol.) also in a water/methanol mixture (75/25, 5 cm$^3$) at 25° C. under constant stirring. The $^{31}$P NMR spectrum of the mixture was recorded at various time intervals as shown in FIG. 19.

X-ray Data Collection and Processing

The crystal data and details of data collection are given in Table 1 for complexes 3 and 5, respectively. Clear colorless crystals of 3 suitable for X-ray diffraction were obtained from slow evaporation of methanol at room temperature, with water as a solvate molecule. Clear colorless crystals of 5 suitable for X-ray diffraction were obtained from methanol/diethyl ether at −20° C. Intensity data were collected on a Siemens SMART CCD system using the omega scan mode. Data were corrected for absorption using the program SADABS which is based on the method of (Blessing, 1995). Crystal decay was less than one percent and a correction deemed unnecessary. The programs used for the crystallographic computations are reported in (Gabe et al., 1989; Johnson, 1976; Le Page, 1988; Le Page and Gabe, 1979). Atomic coordinates and their equivalent isotropic displacement coefficients for both complexes 3 and 5 are listed in Tables 2 and 3, respectively.

Results and Discussion

I. Reactions of 1,2-bis(bis(hydroxymethyl)phosphino) benzene (HMPB, 1) and 1,2-bis(bis)hydroxymethyl) phosphino)ethane (HMPE, 2) with NaAuCl$_4$:

Interaction of an aqueous solution of sodium tetrachloroaurate with five equivalents of the bisphosphines 1 and 2 afforded the new gold(I) complexes [Au{(HOH$_2$C)$_2$PC$_6$H$_4$P(CH$_2$OH)$_2$}$_2$]$^+$ (3) and [Au{(HOH$_2$C)$_2$PCH$_2$CH$_2$P(CH$_2$OH)$_2$}$_2$]$^+$ (4) (Scheme 1 as shown in FIG. 11), respectively, in near quantitative yields. The use of excess ligand for these reactions becomes apparent as the phosphines reduces Au(III) in NaAuCl$_4$ to Au(I) in the corresponding complexes 3 and 4.

The molecular constitutions of complexes 3 and 4 were confirmed by fast atom bombardment mass spectroscopy ([M]$^+$, m/z=721.0699 for 3; m/z=625.0720 for 4). The $^{31}$P NMR spectra of complexes 3 and 4 consisted of singlets at 12.2 and 18.6 ppm, respectively indicating a pronounced downfield shift compared to the parent ligands 1 and 2 (Δδ=4.34 for 3 and 43.7 for 4). It is interesting to note that in the $^1$H NMR spectra, of both complexes 3 and 4, the coupling of the phosphorus and the methylene protons (of —CH$_2$OH), across two bonds, is absent. Also, that the methylene protons in complexes 3 and 4 (due to —CH$_2$OH groups) resonate as AB quarters ($^2J_{HH}$=12.92 Hz for 3 and 13.53 Hz for 4) suggesting diastereotopic nature of these hydrogens. The final confirmation of the structure of complex 3 has come from X-ray crystallographic investigations of the single crystals as outlined in the foregoing sections.

II. Reactions of 1,2-bis(bis(hydroxymethyl)phosphino) benzene (HMPB, 1) and 1,2-bis(bis(hydroxymethyl) phosphino)ethane (HMPE, 2) with AuClPPh$_3$ under Aqueous-Organic Biphasic Media:

1,2-bis(bis(hydroxymethyl)phosphino)benzene (1), in water, upon interaction with one equivalent of AuClPPh$_3$, in dichloromethane, produced the cationic complex 3 in near quantitative yields (Scheme 2 of FIG. 12). The $^{31}$P, $^1$H NMR and mass spectrometric data were identical to the product obtained from the reaction of 1 with sodium tetrachloroaurate as described in Scheme 1 of FIG. 11. In sharp contrast, the reaction of 2 with AuClPPh$_3$, under biphasic conditions, produced a different product (Scheme 2 of FIG. 12) as compared to its reaction with sodium tetrachloroaurate (Scheme 1 of FIG. 11). The mass spectrometric data of this new product ([M]$^+$, m/z=857.0066) indicated it to be a dinuclear gold(I) complex [Au$_2${(HOH$_2$C)$_2$PCH$_2$CH$_2$P(CH$_2$)H)$_2$}$_2$]$^{2+}$ (5) as formulated in Scheme 2 of FIG. 12. The $^{31}$P NMR spectrum of 5 which consisted of a singlet at 36.9 ppm indicates a pronounced downfield shift (Δδ=62 ppm) compared to the mononuclear complexes 3 and 4. The final confirmation of the molecular constitution of 5 was obtained from its X-ray crystal structure as discussed in the foregoing sections.

It is important to recognize that in the reactions of 1 (or 2) with AuClPPh$_3$ under biphasic conditions (Scheme 2 of FIG. 12) typically, 95–98% of the metal precursor from the dichloromethane phase was transferred into the phosphine-containing aqueous phase in approximately thirty minutes upon simple stirring of the respective solutions. Separation and evaporation of the aqueous phases from the reactions produced the mononuclear gold(I) complex 3 and the dinuclear complex 5, respectively.

Figure 13:
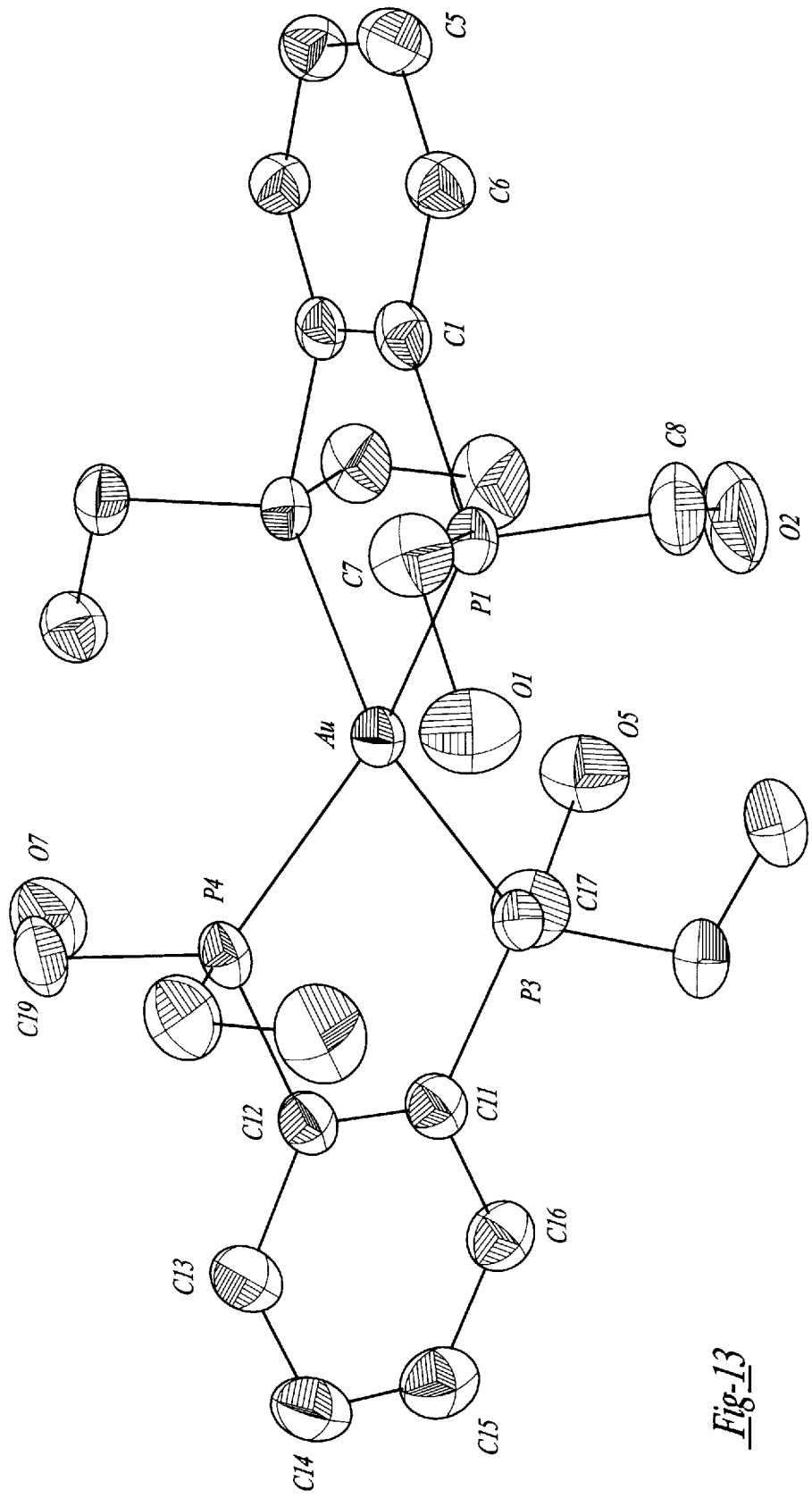
FIG. 13 illustrates an ORTEP drawing of complex 3.

III. X-ray Crystallographic Investigations of [Au{(HOH$_2$C)$_2$PC$_6$H$_4$P(CH$_2$OH)$_2$}$_2$]$^+$ (3) and [Au$_2${(HOH$_2$C)$_2$PCH$_2$CH$_2$P(CH$_2$OH)$_2$}$_2$]$^{2+}$ (5):

The molecular structure of complex 3 was further confirmed by X-ray crystallography. An ORTEP diagram of the cationic molecule is shown in FIG. 13, and the selected bond distances and bond angles are listed in Table 4. The asymmetric unit consists of the complex cation [Au{(HOH$_2$C)$_2$PC$_6$H$_4$P(CH$_2$OH)$_2$}$_2$]$^+$, one non-coordinating chloride counter ion and a single water molecule. The gold atom is coordinated to four phosphorus atoms in a distorted tetrahedral arrangement where the chelate ring angles are 86.44° and 86.66° for P1-Au-P1$^a$ and P2-Au-P4, respectively. These are shorter then ideal angles and are compensated by larger non-chelated angles P1-Au-P3, P1-Au-P4, P1$^a$-Au-P3 and P1$^a$-Au-P4 with an average of 122.00°. The Au—P distances range from 2.354 to 2.368 Å with an average of 2.367 Å and are consistent with the previously reported values for Au—P bonds (Bates et al., 1984; Bemers-Price et al., 1984).

Tetrahedral coordination with gold(I), although less prevalent, has been achieved with monodentate phosphines (e.g.; $\{Au(PMePh_2)_4\}[BF_4]$ and $[(TPA)_4Au][PF_6]$ where TPA is 1,3,5-triaza-7-phosphaadamantane) (Elder et al., 1981; Forward et al., 1996). Complexes 3 and 4 provide rare examples of gold(I) complexes consisting of coordination of bisphosphine in a tetrahedral geometry similar to that found for the bisphosphine complex $[Au(DPPE)_2]^+$ (Bates and Waters, 1984; Berners-Price et al., 1984).

Crystals of complex 5 suitable for X-ray diffraction analysis were produced from methanol/ether solution (at −20° C.). The asymmetric unit comprises of the dicationic complex $[Au_2\{(HOH_2C)_2PCH_2CH_2P(CH_2)H)_2\}_2]^{2+}$ with two crystallographically independent molecules and two chloride counter ions per molecule. The ORTEP diagrams of the two molecules are shown in FIG. 14, and the selected bond distances and bond angles are listed in Table 5. Both of the gold atoms are coordinated to two phosphorus atoms in a near linear environment with bond angles of 176.36, 177.24, 177.09 and 176.53 for P1a-Au1a-P3a, P2a-Au2a-P4a, P1b-Au1b-P2b, and P2b-Au2b-P4b, respectively. The average Au—P distance in complex 5 is 2.308 Å and is consistent with values previously reported for Au—P bonds (Jaw et al., 1989).

IV. Aurophilicity In $[Au_2\{(HOH_2C)_2PCH_2CH_2P(CH_2OH)_2\}_2]^{2+}$ (5)

The fact that gold(I) centers in complex 5 are bound to only the phosphines and that they are not bridged (by halogens or pseudohalogens) becomes important in the context of determining the extent Au(I)—Au(I) interactions which, sometimes, is referred to as the degree of aurophilicity (Schmidbaur, 1995). X-ray crystallographic data of complex 5 indicated a distance of 2.9324(9) Å (and 2.9478 (9) Å for the second molecule in the asymmetric unit) for the Au—Au interaction. This magnitude for the Au—Au distance is short and suggests the operation of "aurophilic" Au—Au attraction. A Au—Au distance of 2.9265(5) Å reported for $[Au_2(DMPE)_2]Cl_2$ is among the shortest distances noted and suggest significant aurophilic characteristics (Jaw et al., 1989). Classical theory of chemical bonding does not offer an explanation for such strong gold—gold interactions. Recent studies involving relativistic and correlation effects have offered more satisfactory rationale for the "aurophilicity" properties in gold(I) complexes (Pitzer, 1979; Berning et al., unpublished results).

Figure 15:
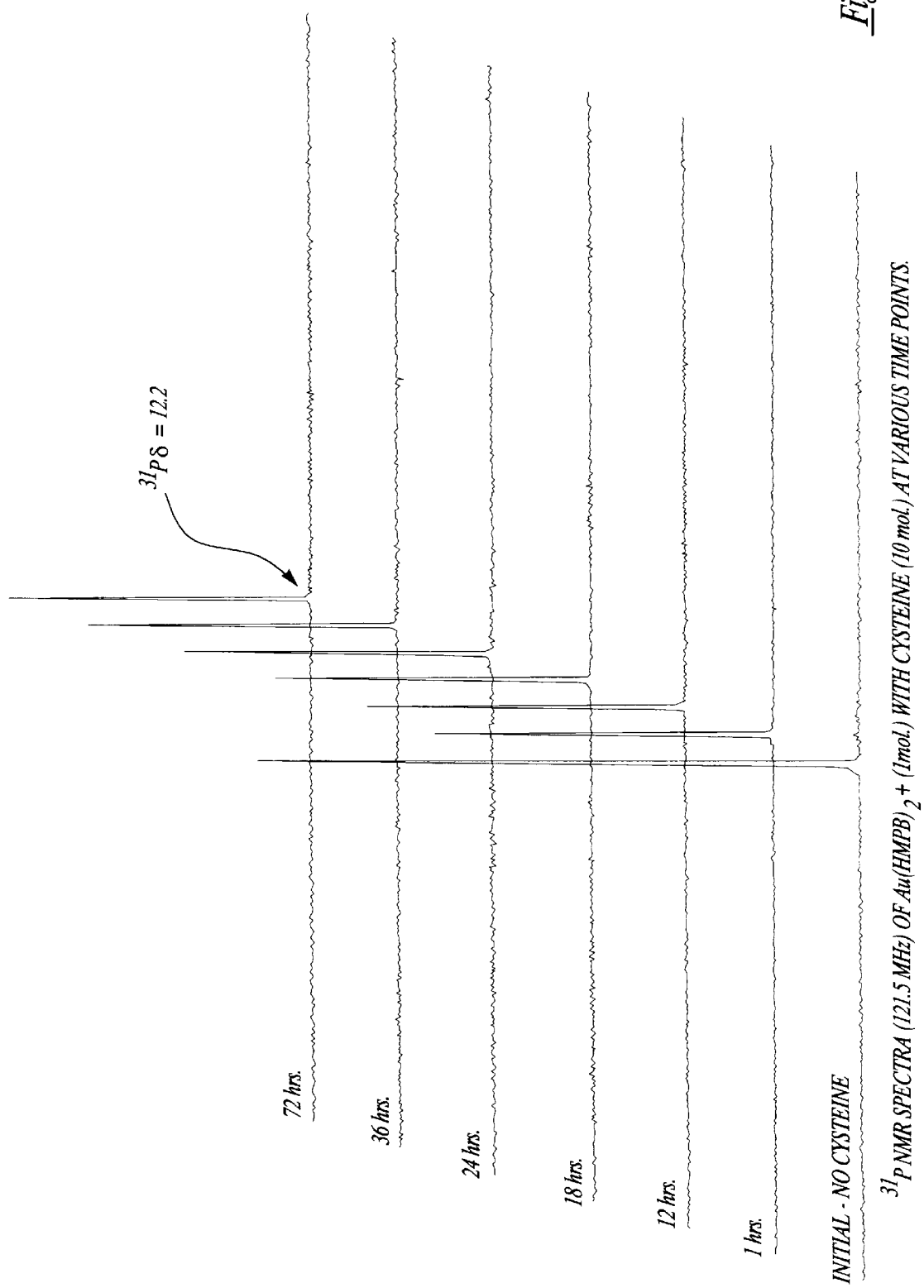
FIG. 15 is a graph illustrating $^{31}$PNMR spectra of $Au(HMPB)_2^+$ at various time points.

V. Stability Studies:

The extent of kinetic inertness of complex 3, in water/methanol, was determined by recording $^{31}P$ NMR spectra of a solution (10 mg/ml) at different time intervals. The results indicate no change in the spectra over seven days and demonstrates the high-stability of complex 3. Additional experiments to understand the in vitro stability of complex 3 were performed by analyzing the stability of complex 3 over a range of temperatures wherein 0.1 ml of $H^{198}AuCl_4$ was added to a solution of HMPB (0.1 ml), diluted with buffer and maintained at the respective temperatures in a dry bath incubator (Fisher Scientific) over time. The results of these studies are shown in Table 8 and 9. Further experiments demonstrating the in vitro stability of complex 3 were performed by analyzing the stability by challenging their aqueous solutions for transchelation with cysteine as shown in Table 10. Typically, aqueous solutions of complex 3 were allowed to interact with approximately ten fold excess of cysteine (in water). The aliquots of this mixture were monitored by $^{31}P$ NMR spectroscopy. It is remarkable to note that no detectable decomposition occurred over seventy-two hours as shown in FIG. 15.

Conclusions

The coordination chemistry of hydroxymethyl phosphines 1 and 2 with $NaAuCl_4$ or $AuClPPh_3$ offers opportunities for the development of water-soluble gold complexes with diverse mono- (e.g. 3 and 4) and bimetallic (e.g. 5) structural characteristics. The high kinetic inertness of this new class of gold complexes in water and also in the presence of excess cysteine may be attributed to the presence of hydroxymethyl substitutents around the metal center. Presumably, electronic replusions between the hydroxymethyl substitutents (present in 3–5) and nucleophiles (—OH or —SH) will keep the metal center well shielded from nucleophilic attack. Preliminary studies on the radiochemical investigation with Au-198 have indicated that ligands 1 and 2 produce complexes in high yields. Further, these complexes of 1 and 2 with Au-198 have demonstrated excellent in vitro and in vivo (Sprague-Dawley rats) stabilities as shown Tables 6 and 7.

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

TABLE 1

Crystal Data for Complexes 3 and 5

| | | |
|---|---|---|
| Formula | $C_{20}H_{32}ClO_8P_4AuH_2O$ | $C_{12}H_{32}Cl_2O_8P_4Au_2$ |
| space group | $P\ 2_1/m$ | $C\ 2/c$ |
| fw | 774.80 | 893.12 |
| a,Å | 9.8715(5) | 29.7128(14) |
| b,Å | 9.9465(5) | 16.7062(8) |
| c,Å | 14.5621(8) | 22.3762(11) |
| α,deg | 90.0 | 90.0 |
| β,deg | 106.5930(10) | 117.6970(10) |
| γ,deg | 90.0 | 90.0 |
| T,K | 295(2) | 295(2) |
| λ,Å | 0.70930 | 0.70930 |
| Z | 2 | 16 |
| F(000) | 764 | 6720 |
| V,$Å^3$ | 1370.27(12) | 9834.6(8) |
| $\rho_{calc}$, g/$cm^3$ | 2.413 | 1.878 |
| $\rho_{obsd}$, g/$cm^3$ | not measured | not measured |
| μ, $mm^{-1}$ | 5.72 | 12.39 |
| $R_1$, $Rw^a$ | 0.032, 0.050 | 0.051, 0.072 |

$^aR_1 = \Sigma(\||F_o| - |F_c|\|)/\Sigma(|F_o|); Rw = [[\Sigma w(|Fo| - |Fc|)^2)/\Sigma w(|Fo|)2]]^{1/2}$

TABLE 2

Atomic Parameters x,y,z and $B_{eq}$ for Complex 3

| | x | y | z | $B_{eq}$ |
|---|---|---|---|---|
| Au | 0.79431(2) | 1/4 | 0.216145(15) | 1.948(12) |
| P1 | 0.96181(12) | 0.41306(11) | 0.29552(8) | 1.92(4) |
| P3 | 0.6876(2) | 1/4 | 0.04946(12) | 1.91(6) |

TABLE 2-continued

Atomic Parameters x,y,z and $B_{eq}$ for Complex 3

| | x | y | z | $B_{eq}$ |
|---|---|---|---|---|
| P4 | 0.5614(2) | 1/4 | 0.23235(12) | 2.14(6) |
| O1 | 0.7980(4) | 0.6148(4) | 0.3193(3) | 3.72(17) |
| O2 | 1.0777(5) | 0.4527(5) | 0.1528(3) | 4.68(22) |
| O5 | 0.8560(5) | 0.4120(5) | -0.0111(3) | 4.93(22) |
| O7 | 0.5298(5) | 0.5179(5) | 0.2570(4) | 4.25(21) |
| C1 | 1.1108(5) | 0.3209(4) | 0.3734(3) | 1.98(16) |
| C6 | 1.3426(5) | 0.3206(6) | 0.4879(4) | 2.98(21) |
| C5 | 1.288(5) | 0.3894(5) | 0.4317(4) | 2.51(18) |
| C7 | 0.9114(6) | 0.5360(5) | 0.3758(4) | 2.84(19) |
| C8 | 1.0456(6) | 0.5242(6) | 0.2267(4) | 3.18(21) |
| C11 | 0.4971(7) | 1/4 | 0.0307(5) | 2.3(3) |
| C12 | 0.4417(7) | 1/4 | 0.1104(5) | 2.2(3) |
| C13 | 0.2955(8) | 1/4 | 0.0940(6) | 3.0(3) |
| C14 | 0.2045(8) | 1/4 | 0.0002(7) | 3.6(3) |
| C15 | 0.2607(9) | 1/4 | -0.0773(6) | 3.5(3) |
| C16 | 0.4045(8) | 1/4 | -0.0631(5) | 3.0(3) |
| C17 | 0.7120(6) | 0.3945(6) | -0.0216(4) | 3.71(24) |
| C19 | 0.4980(6) | 0.3919(6) | 0.2918(4) | 3.16(22) |
| Cl | 0.2514(3) | 3/4 | 0.46163(23) | 4.97(12) |
| OW | 0.3780(9) | 3/4 | 0.2856(7) | 6.7(5) |

$B_{eq}$ is the Mean of the Principal Axes of the Thermal Ellipsoid

TABLE 3

Atomic Parameters x,y,z and $B_{eq}$ for Complex 5

| | x | y | z | $B_{eq}$ |
|---|---|---|---|---|
| Au1A | 0.274541(21) | 0.07932(4) | 0.013204(25) | 3.03(3) |
| Au2A | 0.218081(20) | -0.07075(4) | -0.007032(25) | 2.96(3) |
| P1A | 0.33321(13) | 0.03063(22) | 0.11687(18) | 3.27(17) |
| P2A | 0.21544(14) | -0.05704(24) | 0.09373(18) | 3.51(19) |
| P3A | 0.21208(14) | 0.12732(22) | -0.08805(18) | 3.35(18) |
| P4A | 0.21649(14) | -0.08486(22) | -0.11098(17) | 3.06(18) |
| O1A | 0.3854(4) | -0.1028(6) | 0.1782(5) | 5.1(6) |
| O2A | 0.4148(6) | 0.0971(11) | 0.1190(8) | 10.9(12) |
| O3A | 0.1340(6) | 0.0290(12) | 0.0408(9) | 14.8(15) |
| O4A | 0.1804(5) | -0.1285(8) | 0.1739(6) | 7.2(8) |
| O5A | 0.1846(4) | 0.2616(6) | -0.1660(6) | 6.0(7) |
| O6A | 0.1525(10) | 0.1486(15) | -0.0318(12) | 9.3(7) |
| O6'A | 0.1319(14) | 0.0560(22) | 0.0836(17) | 8.7(10) |
| O7A | 0.2745(4) | -0.0702(7) | -0.1747(6) | 6.1(8) |
| O8A | 0.2212(8) | -0.2475(13) | -0.1140(11) | 5.1(5) |
| O8'A | 0.1879(8) | 0.2404(13) | -0.1045(10) | 4.6(4) |
| C1A | 0.3112(5) | 0.0227(9) | 0.1803(7) | 3.5(7) |
| C2A | 0.2762(6) | -0.0516(10) | 0.1704(7) | 4.4(9) |
| C3A | 0.3573(5) | -0.0685(8) | 0.1124(7) | 3.6(7) |
| C4A | 0.3905(6) | 0.0911(9) | 0.1596(8) | 4.3(8) |
| C5A | 0.1814(6) | 0.0330(12) | 0.0969(8) | 6.1(11) |
| C6A | 0.1821(6) | -0.1397(11) | 0.1093(9) | 5.8(11) |
| C7A | 0.2027(6) | 0.0731(9) | -0.1652(6) | 4.0(8) |
| C8A | 0.1797(5) | -0.0097(9) | -0.1753(7) | 3.9(8) |
| C9A | 0.2243(7) | 0.2293(10) | -0.1021(8) | 5.3(11) |
| C10A | 0.1475(7) | 0.1296(11) | -0.0962(9) | 6.1(12) |
| C11A | 0.2792(6) | -0.0802(9) | -0.1086(8) | 4.5(9) |
| C12A | 0.1877(6) | -0.1833(9) | -0.1501(7) | 4.7(9) |
| Au1B | 0.034210(21) | -0.17910(4) | 0.01176(3) | 3.35(3) |
| Au2B | -0.024190(22) | -0.32903(4) | -0.01373(3) | 3.27(3) |
| P1B | 0.03661(15) | -0.16583(24) | 0.11550(18) | 3.53(19) |
| P2B | 0.03329(15) | -0.38211(24) | 0.08918(19) | 3.85(21) |
| P3B | 0.03626(14) | -0.19259(23) | -0.08964(18) | 3.49(19) |
| P4B | -0.08272(13) | 0.28378(21) | -0.11917(17) | 3.03(17) |
| O1B | -0.0234(6) | -0.1683(10) | 0.1759(7) | 9.8(12) |
| O2B | 0.0486(12) | 0.0081(19) | 0.1239(16) | 9.5(9) |
| O2'B | 0.0817(13) | 0.0873(20) | 0.2346(16) | 11.0(10) |
| O3B | 0.0508(5) | -0.5130(8) | 0.1671(6) | 7.5(9) |
| O4B | 0.0934(7) | -0.4538(11) | 0.0454(8) | 6.4(11) |
| O4'B | 0.625(3) | 0.088(4) | 0.159(3) | 14.4(22) |
| O5B | 0.1218(9) | -0.2764(13) | -0.0460(11) | 9.7(6) |
| O5'B | 0.0493(16) | -0.349(3) | -0.0911(21) | 6.9(11) |
| O6B | 0.0758(5) | -0.1227(8) | -0.1630(6) | 6.4(8) |
| O7B | -0.1456(4) | -0.1590(6) | -0.1816(5) | 5.2(6) |

TABLE 3-continued

Atomic Parameters x,y,z and $B_{eq}$ for Complex 5

| | x | y | z | $B_{eq}$ |
|---|---|---|---|---|
| O8B | -0.1449(6) | -0.4010(10) | -0.1243(9) | 11.7(13) |
| C1B | 0.0693(8) | -0.2456(10) | 0.1781(7) | 6.3(12) |
| C2B | 0.0441(7) | -0.3242(10) | 0.1644(7) | 5.2(11) |
| C3B | -0.0275(7) | -0.1573(14) | 0.1110(10) | 7.2(13) |
| C4B | 0.0714(7) | -0.0739(12) | 0.1629(8) | 5.7(11) |
| C5B | 0.0142(6) | -0.4819(10) | 0.1040(9) | 5.6(10) |
| C6B | 0.0981(6) | -0.3981(12) | 0.0926(10) | 6.4(11) |
| C7B | -0.0225(6) | -0.1897(8) | -0.1637(7) | 3.9(8) |
| C8B | -0.0579(5) | -0.2639(9) | -0.1784(6) | 3.8(8) |
| C9B | 0.0681(7) | -0.2831(10) | -0.0989(8) | 5.4(10) |
| C10B | 0.0721(7) | -0.1146(11) | -0.1043(8) | 5.7(10) |
| C11B | -0.1129(6) | -0.1914(9) | -0.1169(7) | 4.3(8) |
| C12B | -0.1338(6) | -0.3558(9) | -0.1662(7) | 4.6(9) |
| C11 | 0 | 0.9965(4) | 1/4 | 7.9(6) |
| C12 | 0 | 0.4315(5) | 1/4 | 6.4(4) |
| C13 | 0.25719(19) | 0.2266(4) | 0.24472(23) | 7.0(3) |
| C14 | 0.1436(3) | -0.6914(4) | 0.0051(3) | 7.5(4) |
| C15 | 0.2006(4) | -0.2586(6) | 0.0040(5) | 8.3(6) |
| C16 | 0.0372(5) | 0.0077(10) | 0.0044(7) | 8.7(4) |
| C17 | 0.3876(10) | 0.0487(15) | -0.0008(12) | 6.9(6) |

$B_{eq}$ is the Mean of the Principal Axes of the Thermal Ellipsoid

TABLE 4

Selected Bond Distances (Å) and Angles (deg) for 3

| Au-P1 | 2.3683(11) | Au-P3 | 2.354(2) |
|---|---|---|---|
| Au-P1[a] | 2.3683(11) | Au-P4 | 2.378(2) |
| P1-Au-P1[a] | 86.44(4) | P1a-Au-P3 | 123.21(4) |
| P1-Au-P3 | 123.21(4) | P1a-Au-P4 | 102.78(4) |
| P1-Au-P4 | 120.78(4) | P3-Au-P4 | 86.66(6) |

[a]atom at x, 0.5 − y, z

TABLE 5

Selected Bond Distances (Å) and Angles (deg) for 5

| Au1a-P1a | 2.307(3) | Au1b-P1b | 2.300(4) |
|---|---|---|---|
| Au1a-P3a | 2.305(4) | Au1b-P3b | 2.309(4) |
| Au2a-P2a | 2.304(4) | Au2b-P2b | 2.313(4) |
| Au2a-P4a | 2.316(3) | Au2b-P4b | 2.313(3) |
| P1a-Au1a-P3a | 176.36(14) | P1b-Au1b-P3b | 177.09(13) |
| P2a-Au2a-P4a | 177.24(13) | P2b-Au2b-P4b | 176.53(14) |

[a]atom at symmetry position 1/2 − x, 1/2 − y, −z
[b]atom at symmetry position 1/2 + x, 1/2 + y, z

TABLE 6

Biodistribution of $^{198}$Au—[(CH$_2$OH)$_2$P—C$_6$H$_4$-P(CH$_2$OH)$_2$] Complex in Anesthetized Rats (N = 5)

| | Percent Injected Dose (ID) per Organ[b] | | |
|---|---|---|---|
| Organ (% Dose) | $^{198}$Au—HMPB 15 min (n = 5) | $^{198}$Au—HMPB 1 hr (n = 5) | $^{198}$Au—HMPB 2 hr (n = 5) |
| Brain | 0.04 ± 0.01 | 0.01 ± 0.00 | 0.01 ± 0.00 |
| Blood | 3.92 ± 0.55 | 2.07 ± 0.42 | 1.71 ± 0.10 |
| Heart | 0.07 ± 0.01 | 0.03 ± 0.00 | 0.03 ± 0.00 |
| Lung | 0.34 ± 0.06 | 0.16.± 0.03 | 0.19 ± 0.02 |
| Liver | 14.88 ± 0.77 | 9.40 ± 1.93 | 8.23 ± 1.32 |
| Spleen | 0.04 ± 0.00 | 0.02 ± 0.00 | 0.03 ± 0.00 |
| Lg. Intestine | 0.47 ± 0.08 | 0.31 ± 0.03 | 0.29 ± 0.03 |
| Sm. Intestine | 25.91 ± 2.26 | 40.55 ± 2.33 | 39.60 ± 2.30 |
| Kidneys | 3.23 ± 0.73 | 1.91 ± 0.19 | 2.16 ± 0.54 |
| Bladder | 24.84 ± 3.26 | 36.94 ± 2.92 | 40.58 ± 0.33 |
| Muscle | 0.04 ± 0.00 | 0.01 ± 0.00 | 0.01 ± 0.00 |

TABLE 6-continued

Biodistribution of $^{198}$Au—[(CH$_2$OH)$_2$P—C$_6$H$_4$—P(CH$_2$OH)$_2$] Complex in Anesthetized Rats (N = 5)

| | Percent Injected Dose (ID) per Organ[b] | | |
|---|---|---|---|
| Organ (% Dose) | $^{198}$Au—HMPB 15 min (n = 5) | $^{198}$Au—HMPB 1 hr (n = 5) | $^{198}$Au—HMPB 2 hr (n = 5) |
| Pancreas | 0.31 ± 0.11 | 0.19 ± 0.05 | 0.19 ± 0.04 |
| Carcass | 28.10 ± 2.31 | 9.27 ± 1.30 | 7.99 ± 0.95 |

[a]Sprague-Dawley rats (180—240 g) anesthetized with Na-pentobarbital (50 mg/kg-IP) were injected intravenously.
[b]% ID/organ values are mean ± SD; n = 5 for each group; % ID in whole blood estimated assuming whole blood volume is 6.5 % of body weight.

TABLE 7

Biodistribution of $^{198}$Au—[(CH$_2$OH)$_2$P—CH$_2$—CH$_2$—P(CH$_2$OH)$_2$)] Complex in Anesthetized Rats [a] as a Function of Time (n = 5)

| | Percent Injected Dose (ID) per Organ[b] | | |
|---|---|---|---|
| Organ (% Dose) | ™ Au—HMPE 15 min (n = 5) | $^{198}$Au—HMPE 1 hr (n = 5) | $^{198}$Au—HMPE 2 hr (n = 5) |
| Brain | 0.09 ± 0.01 | 0.07 ± 0.01 | 0.09 ± 0.01 |
| Blood | 13.45 ± 0.75 | 11.00 ± 0.66 | 11.11 ± 1.59 |
| Heart | 0.22 ± 0.02 | 0.18 ± 0.02 | 0.19 ± 0.02 |
| Lung | 0.81 ± 0.19 | 0.82 ± 0.14 | 0.77 ± 0.23 |
| Liver | 4.25 ± 0.37 | 3.47 ± 0.39 | 3.05 ± 0.50 |
| Spleen | 0.12 ± 0.00 | 0.10 ± 0.00 | 0.09 ± 0.00 |
| Lg. Intestine | 0.86 ± 0.11 | 0.79 ± 0.13 | 0.73 ± 0.11 |
| Sm. Intestine | 3.24 ± 0.33 | 4.13 ± 0.39 | 4.08 ± 0.47 |
| Kidneys | 5.36 ± 1.13 | 5.03 ± 0.77 | 4.84 ± 0.88 |
| Bladder | 33.08 ± 2.09 | 41.24 ± 2.81 | 43.58 ± 3.22 |
| Muscle | 0.07 ± 0.00 | 0.06 ± 0.00 | 0.07 ± 0.00 |
| Pancreas | 0.33 ± 0.02 | 0.34 ± 0.05 | 0.34 ± 0.04 |
| Carcass | 49.36 ± 3.08 | 41.84 ± 2.23 | 40.17 ± 2.23 |

[a]Sprague-Dawley rats (180—240 g) anesthetized with Na—pentobarbital (50 mg/kg—IP) were injected intravenously.
[b]% ID/organ values are mean ± SD; n = 5 for each group; % ID in whole blood estimated assuming whole blood volume is 6.5% of body weight.

TABLE 8

™ Au—HMPB Stability at Various Temperatures

| Time (hrs.)/Temp. (°C.) | 25 | 40 | 60 | 80 |
|---|---|---|---|---|
| 0.5 | 98.4 ± 1.4 | 98.4 ± 1.4 | 97.9 ± 2.1 | 98.6 ± 1.3 |
| 1 | 98.8 ± 1.9 | 99.1 ± 1.3 | 98.9 ± 1.5 | 99.4 ± 0.8 |
| 3 | 99.2 ± 1.5 | 98.8 ± 1.5 | 99.0 ± 1.8 | 97.7 ± 0.8 |
| 5 | 99.2 ± 1.4 | 99.0 ± 0.9 | 98.1 ± 3.3 | 92.0 ± 2.7 |
| 7 | 99.0 ± 1.7 | 99.3 ± 1.1 | 99.0 ± 0.9 | 92.0 ± 3.8 |
| 24 | 99.3 ± 1.3 | 99.1 ± 1.4 | 99.2 ± 1.5 | 90.3 ± 2.8 |

H$^{198}$AuCl$_4$ (0.1 ml) was added to a solution of HMPB (0.1 ml, 10 mg/ml) and diluted with buffer (0.8 ml). The solutions were maintained at their respective temperatures throughout the study in a Fisher dry bath incubator.

TABLE 9

$^{198}$Au—HMPB Stability at Various Temperatures

| Time (hrs.)/Temp. (°C.) | 25 | 40 | 60 | 80 |
|---|---|---|---|---|
| 0.5 | 98.2 ± 1.5 | 98.9 ± 1.3 | 99.2 ± 1.4 | 99.1 ± 1.6 |
| 1 | 99.1 ± 1.4 | 98.6 ± 1.8 | 98.9 ± 0.9 | 99.3 ± 0.9 |
| 3 | 98.8 ± 0.9 | 99.4 ± 0.7 | 97.5 ± 1.9 | 98.9 ± 1.6 |
| 5 | 98.8 ± 1.2 | 98.8 ± 1.2 | 96.4 ± 2.5 | 85.5 ± 3.2 |
| 7 | 99.3 ± 1.6 | 99.1 ± 1.3 | 99.2 ± 1.3 | 64.8 ± 2.8 |
| 24 | 99.1 ± 1.1 | 98.9 ± 1.1 | 97.8 ± 1.9 | 40.8 ± 2.5 |

H$^{198}$AuCl$_4$ (0.1 ml) was added to a solution of HMPB (0.1 ml, 10 mg/ml) and diluted with water (0.8 ml). The solutions were maintained at their respective temperatures throughout the study in a Fisher dry bath incubator.

TABLE 10

$^{198}$Au–HMPB Cysteine Challenge

| Times (hrs.)/ | 10 times excess | | 100 times excess | |
|---|---|---|---|---|
| Cysteine conc. | natural pH | pH 7.4 | natural pH | pH 7.4 |
| 0.5 | 99.6 ± 0.8 | 99.2 ± 1.3 | 99.1 ± 1.5 | 96.4 ± 3.2 |
| 1 | 99.5 ± 1.2 | 89.6 ± 1.8 | 98.5 ± 1.8 | 93.7 ± 3.3 |
| 3 | 99.3 ± 1.3 | 88.4 ± 2.1 | 97.4 ± 2.2 | 89.1 ± 1.2 |
| 5 | 99.0 ± 1.4 | 89.3 ± 1.9 | 97.3 ± 2.9 | 88.7 ± 2.5 |
| 7 | 98.9 ± 1.8 | 88.2 ± 1.5 | 95.8 ± 1.7 | 88.8 ± 1.6 |
| 24 | 99.2 ± 1.5 | 90.3 ± 3.2 | 97.6 ± 2.1 | 91.2 ± 2.9 |

H198 AuCl$_4$ (0.1 ml) was added to a solution of HMPB (0.1 ml, 10 mg/ml) and diluted with water or buffer (0.8 ml) containing the corresponding amount of cysteine.

REFERENCES CITED

Bates and Waters, (1984) *Inorg. Chim. Acta*, 81:151.
Berglof et al., (1978) *J. Rheumatol.*, 5:68.
Berners-Price et al., (1984) *J. Chem. Soc. Dalton Trans.*, 969.
Beming et al., (1996) *Nucl Med. Biol.*, 23:617.
Beming, D. E.; Katti, K. V.; Sing, P. R.; Higgenbotham, C.; Reddy, V. S; Volkert, W. A., (unpublished results)
Berning, D. E.; Tweedy, L.; Higgenbotham, C.; Katti, K. V.; Volkert, W. A.; (unpublished results).
Blessing, (1995) *Acta Crystallogr.*, A51:33.
Elder et al., (1981) *J. Chem. Soc. Chem. Commun.*, 900.
Forward et al., (1996) *Inorg. Chem.*, 35:16.
Fricker S. P., (1996) *Transition Met. Chem*, 21:377.
Gabe et al., (1989) *J. Appl. Cryst.*, 22:384.
*International Table for X-ray Crystallograpy*; Kynoch Press: Birmingham, England, (1974), Vol. 4.
Jaw et al., (1989) *Inorg. Chem.*, 28:1028.
Johnson (1976) in *ORTEP—A Fortran Thermal Ellipsoid Plot Program*, Technical Report ORNL-5138, Oak Ridge National Laboratory: Oak Ridge, Tenn.
Le Page (1988), *J. Appl. Cryst.*, 21:983.
Le Page et al., (1979) *J. Appl. Cryst.*, 12:464.
Mirabelli et al., (1985) *Cancer Res.*, 45:32.
Pitzer (1979) *Acc. Chem. Res.*, 12:271.
Pyykko (1988) *Chem. Rev.*, 88:563.
Reddy et al., (1996a) *J. Chem. Soc., Dalton Trans.*, 1301.
Reddy et al., (1996b) *Inorg. Chem.*, 35:1753.
Rush et al., (1987) *Toxicologist*, 7:59.
Schubiger et al., (1996) *Bioconjugate Chem.*, 7:165.
Shi et al., (1996) *Inorg. Chem.*, 35:2742.
Schmidbaur, (1995) *Chem. Soc. Rev.*, 391.
Simon et al., (1981) *Cancer Res.*, 41:94.
Smith et al., *Inorg. Chem.*, (submitted for publication).
Volkert et al., (1991) *J. Nucl. Med.*, 32:174.

What is claimed is:

1. A complex for use as a diagnostic or therapeutic pharmaceutical, said complex comprising:

a ligand comprising at least one hydroxyalkyl phosphine donor group bound to a gold atom to form a gold-ligand complex that is stable in aqueous solutions containing oxygen, serum and other body fluids, wherein said gold atom is an isotope selected from the group including γ and β emitting isotopes.

2. A complex as set forth in claim 1, wherein said metallic gold isotope is a radionuclide selected from the group including $^{198}$Au and $^{199}$Au.

3. A complex as set forth in claim 1, wherein said ligand is monodentate of the formula:

P(AOH)$_3$ wherein A is —CH$_2$—, —C$_2$H$_4$—, or iso- or normal-C$_3$H$_6$—.

4. A complex as set forth in claim 1 including other donor atoms or groups on the same ligand as a donor hydroxyalkyl phosphine group combined with said gold-ligand complex.

5. A complex as set forth in claim 4, wherein said donor group contains N, S, O, or P atoms for coordinating said gold.

6. A complex as set forth in claim 5, wherein said donor group further includes amines, amides, thiols, carboxyls, and hydroxyls for coordinating said gold.

7. A complex as set forth in claim 1, wherein the ratio of ligand to gold is greater than or equal to 1:1.

8. A complex as set forth in claim 1, wherein said ligand is bidentate of the formula:

(HOA)$_2$P—X—P(AOH)$_2$ wherein A is —CH$_2$—, —C$_2$H$_4$—, or iso- or normal-C$_3$H$_6$—; and X is —(CH$_2$)$_n$— where n=1–4, —CH$_2$CHR—, —CH$_2$CHRCH$_2$—, —CHRCH$_2$CH$_2$—, or R'-aromatic where R' is H, an alkyl group of C$_1$–C$_4$, an aromatic group, —OH, —SH, —NH$_2$, —COOH, activated esters, N-hydroxysuccinimides, benzyl isothiocyanate, alkyl halides, or cyclohexyldiimide.

9. A method for delivering a radiation dose to cancer tissue or arthritic site; said method comprising the steps of: administering an effective amount of a complex comprising a ligand comprising at least one hydroxyalkyl phosphine group bound to a gold atom to form a gold-ligand complex that is stable in aqueous solutions containing oxygen, serum and other body fluids, wherein said gold atom is a isotope selected from the group including γ and β emitting isotopes.

10. A method as set forth in claim 9, wherein said metallic isotope is a radionuclide selected from the group including $^{189}$Au and $^{199}$Au.

11. A method as set forth in claim 9, wherein said ligand is monodentate of the formula:

P(AOH)$_3$ wherein A is —CH$_2$—, —C$_2$H$_4$—, or iso- or normal-C$_3$H$_6$—.

12. A method as set forth in claim 9 including a donor group combined with said gold-ligand complex.

13. A method as set forth in claim 12, wherein said donor group contains N, S, O, Ag, or phosphorus atoms for coordinating said gold.

14. A method as set forth in claim 12, wherein said donor group further includes amines, amides, thiols, carboxyls, and hydroxyls for coordinating said gold.

15. A method as set forth in claim 9, wherein the ratio of gold to ligand is greater than or equal to 1:1.

16. A method as set forth in claim 9, wherein said ligand is bidentate of the formula:

(HOA)$_2$P—X—P(AOH)$_2$ wherein A is —CH$_2$—, —C$_2$H$_4$—, or iso- or normal-C$_3$H$_6$—; and X is —(CH$_2$)$_n$— where n=1–4, —CH$_2$CHR—, —CH$_2$CHRCH$_2$—, —CHRCH$_2$CH$_2$—, or R'-aromatic where R' is H, an alkyl group of C$_1$–C$_4$, an aromatic group, —OH, —SH, —NH$_2$, —COOH, activated esters, N-hydroxysuccinimides, benzyl isothiocyanate, alkyl halides, or cyclohexyldiimide.

* * * * *